US008609812B2

(12) United States Patent  
Maurer et al.

(10) Patent No.: US 8,609,812 B2
(45) Date of Patent: Dec. 17, 2013

(54) USE OF β-2-MICROGLOBULIN TO ASSESS GLOMERULAR ALTERATIONS AND DAMAGE IN THE KIDNEY

(75) Inventors: Gerard Maurer, Ruelisheim (FR); Frank Dieterle, Basel (CH); Elias Perentes, Saint Louis (FR); Frank Städtler, Binzen (DE); André Cordier, Basel (CH); Andreas Mahl, Lörrach (DE); Jacky Vonderscher, San Diego, CA (US); Daniel Wahl, Münchenstein (CH); Olivier Grenet, Michelbach le Haut (FR); Daniel Robert Roth, Courroux (CH)

(73) Assignee: Novartis AG, Basel (CH)

( * ) Notice: Subject to any disclaimer, the term of this patent is extended or adjusted under 35 U.S.C. 154(b) by 529 days.

(21) Appl. No.: 12/532,903

(22) PCT Filed: Mar. 25, 2008

(86) PCT No.: PCT/EP2008/053504
§ 371 (c)(1),
(2), (4) Date: Feb. 15, 2010

(87) PCT Pub. No.: WO2008/116867
PCT Pub. Date: Oct. 2, 2008

(65) Prior Publication Data
US 2010/0143956 A1   Jun. 10, 2010

Related U.S. Application Data

(60) Provisional application No. 60/908,094, filed on Mar. 26, 2007.

(51) Int. Cl.
C07K 1/00 (2006.01)

(52) U.S. Cl.
USPC ........................................................ 530/350

(58) Field of Classification Search
USPC ........................................................ 530/350
See application file for complete search history.

(56) References Cited

U.S. PATENT DOCUMENTS

| | | | |
|---|---|---|---|
| 7,700,112 B2 | 4/2010 | Garone | |
| 2004/0219603 A1 | 11/2004 | Devarajan | |
| 2004/0241774 A1 | 12/2004 | Kazuo | |
| 2006/0008804 A1 | 1/2006 | Chibout | |
| 2008/0171396 A1* | 7/2008 | Fung et al. | 436/86 |
| 2009/0093010 A1* | 4/2009 | Nickerson et al. | 435/23 |
| 2012/0077708 A1* | 3/2012 | Cooke et al. | 506/12 |

FOREIGN PATENT DOCUMENTS

| | | |
|---|---|---|
| EP | 1 231 469 | 4/2002 |
| JP | 3730919 B1 | 1/2006 |
| RU | 2180965 C1 | 3/2002 |
| WO | 99/15904 A1 | 4/1999 |
| WO | 02/06537 | 1/2002 |
| WO | 2004/005544 A2 | 1/2004 |
| WO | 2004/005934 A2 | 1/2004 |
| WO | 2005/100989 A2 | 10/2005 |
| WO | 2006/056037 | 6/2006 |

OTHER PUBLICATIONS

Marchewka Z. et al. Enzymes in Urine as Markers of Nephrotoxicity of Cytostatic Agents and Aminoglycoside Antibiotics. International Urology and Nephrology 30(3)339-348, 1998.*

Tokuc G. et al. Renal Dysfunctions Secondary to Ifosfamide Treatment in Children. J of Experimental & Clinical Cancer Research 16(2)227-230, Jun. 1997.*

Marchewka, Z, et at., "Enzymes in urine as markers of nephrotoxicity of cytostatic agents and aminoglycoside antibiotics", International Urology and Nephrology, vol. 30, No. 3, pp. 339-348, (1998).

Han Won K of al "Kidney Injury Molecule-I (KIM-1): A novel biomarker for human renal proximal tubule injury" Kidney Int 62:237-244 (2002).

Ito Masayuki et al "Comparison of stability fo $\beta_2$-microglobulin and $\alpha_1$-microglobulin in urine: Molecular marker to the dysfunction of tubular and glomerular" JP J Med Technol 54(7):986-989 (2005), English abstract.

Tassi C et al: "beta-N-Acetylhexosaminidase in the urine. kidney and serum of bromobenzene-intoxicated mice". Clinica Chimica Acta. Elsevier BV. Amsterdam. NL vol, 206. No. 3. Mar. 31, 1992. pp. 231-239.

Mishra J et al: "Identification of neutrophil gelatinase-associated lipocalin as a novel early urinary biomarker for ischemic renal injury", Journal of the American Society of Nephrology. Williams and Wilkins. Baltimore. MD. US. vol , 14. No. 10, Oct. 1, 2003. pp. 2534-2543.

Mishra J et al: "Neutrophil 1-6 Gelatinase-Associated Lipocalin: A Novel Early Urinary Biomarker for Cisplatin Nephrotoxicity". American Journal of Nephrology. S. Karger AG. Basel. CH. vol. 24. May 12, 2004. pp. 307-315.

Bachorzewska-Gajewska H et al: "Neutrophil gelatinase-associated lipocalin (NGAL) correlations with cystatin c. serum creatinine and eGFR in patients with normal serum creatinine undergoing coronary angiography [19]". Nephrology Dialysis Transplantation—Special Issue on Pediatric Overweight 200701 GB LNKD—DOI:10.1093/NDT/GFL408. vol. 22. No. 1. Jan. 2007. pp. 295-296.

Takashi M et al: Urinary 28-kD calbindin-D as a new marker for damage to distal renal tubules caused by cisplatin-based chemotherapy. Urologia Internationalis. vol. 56. No. 3. 1996. pages 174-179.

Yang et al. "Inhibition of calbindin D28K expression by cyclosporin A in rat kidney: the possible pathogenesis of cyclosporin A-induced hypercalciuria" Jan. 1, 1998 9: 1416-1426.

(Continued)

Primary Examiner — Ralph Gitomer
(74) Attorney, Agent, or Firm — Christine McCormack

(57) ABSTRACT

The present invention is directed, in part, to a method of measuring β-2-microglobulin to assess glomerular alteration or damage of the kidney.

7 Claims, 13 Drawing Sheets

(56) References Cited

OTHER PUBLICATIONS

Aicher et al."Decrease in Kidney Calbindin-D 28kDa as a Possible Mechanism Mediating Cyclosporine A- and FK506-induced calciuria and Tubular Mineralization" Jan. 1, 1997 53:723-731.

Eti Serife et al: "Urinary clusterin in chronic nephrotoxicity in the rat" Proceedings of the Society for Experimental Biology & Medicine. Academic Press Inc. New York. US. vol, 202, No. 4. Jan. 1, 1993. pp. 487-490.

Aulitzky W K et al: "Measurement of urinary clusterin as an index of nephrotoxicity" Proceedings of the Society for Experimental Biology & Medicine. Academic Press Inc. New York. US. vol. 199. No. 1., Jan. 1, 1992. pp. 93-96.

Yoshimi Tsuchiya et al: "Investigation on 1-5 urinary proteins and renal mRNA expression in canine renal papillary necrosis induced by nefi racetam". Archives of Toxicology. Springer-Verlag. Berlin. DE. vol. 79. No. 9., Sep. 1, 2005. pp. 500-507.

Darby I A et al: "Vascular expression of clusterin in experiental cyclosporine nephrotoxicity", Experimental Nephrology. Karger. DE., vol. 3. Jan. 1, 1995. pp. 234-239.

Girton R A et al: "Clusterin protects renal tubular epithelial cells from gentamicin-mediated cytotoxicity", American Journal of Physiology. American Physiological Society. United States. vol. 282. No. 4. Part 02. Apr. 1, 2002. pp. F703-F709.

Gunel N et al: "The role of serum cystatin c and TC-99M MAG-3 renal scintigraphy for predicting cisplatin induced nephrotoxicity in cancer patients", European Journal of Cancer. Pergamon Press. Oxford. GB., vol. 37. Apr. 2001. p. S359.

Gunel et al. "Evaluation of serum cystatin C levels and 99m Technetiume mercaptoacetyltriglycine-3 renal scintigraphy for the early detection of cisplatin-induced renal toxicity in cancer patients", Jan.1, 2002. pp. 56-60. Neurology 2002: 756-760.

Tian S et al: "Cystatin C measurement and its practical use in patients with various renal diseases", Clinical Nephrology. Dustri Verlag. Nuenchen-Deisenhofen. DE. vol. 48. No. 2., Jan. 1, 1997. pp. 104-108.

Roy et al. "Increased risk of antituberculosis drug-induced hepatotoxicity in individuals with glutathione S-transferase M1 'null' mutation", Jan. 1, 2001. 16, pp. 1033-1037.

Huang Y S et al: "Genetic polymorphisms of manganese superoxide dismutase", NAD (P) H:quinone oxidoreductase, glutathione S-transferase M1 and T1, and the susceptibility to drug-induced liver injury, Journal of Hepatology. Munksgaard International Publishers. Copenhagen. DK. vol. 47. No. 1. Mar. 6, 2007. pp. 128-134.

V. S. Vaidya: "Urinary kidney injury molecule-1: a sensitive quantitative biomarker for early detection of kidney tubular injury". AJP: Renal Physiology. vol. 290. No. 2. Feb. 1, 2006. pp. F517-F529.

T. Ichimura: "Kidney injury molecule-1: a tissue and urinary biomarker for nephrotoxicant-induced renal injury" AJP: Renal Physiology. vol. 286. No. 3. Mar. 1, 2004 pp. 552F-563.

Devarajan Prasad: "Emerging biomarkers of acute kidney injury'. Contributions to Nephrology Karger. Basel. CH. vol. 156. Jan. 1, 2007. pp. 203-212.

Yokoo et al: "Differential contribution of organic cation transporters. OCT2 and MATE1. in platinum agent-induced nephrotoxicity". Biochemical Pharmacology. Pergamon. Oxford. GB. vol. 74. No. 3. Mar. 12, 2007 pp. 477-487.

Kharasch Evan D et al: "Gene expression profiling of nephrotoxicity from the sevoflurane degradation product fluoromethy1-2.2-difluoro-1-(trifluorometh yl)vinyl ether (compound A) in rats" Toxicological Sciences. Academic Press. San Diego. FL. US. vol. 90. No. 2. Apr. 1, 2006. pp. 419-431.

Brook N R et al: "Cyclosporine and Rapamycin Act in a Synergistic and Dose-Dependent Manner in a Model of Immunosuppressant-Induced Kidney Damage". Transplantation Proceedings. Elsevier Inc. Orlando. FL; US. vol. 37. No. 2. Mar. 1, 2005. pp. 837-838.

Milan Chromek et al: "Matrix Metalloproteinase-9 and Tissue Inhibitor of Metalloproteinases-1 in Acute Pyelonephritis and Renal Scarring." Pediatric Research. vol. 53. No. 4., Apr. 1, 2003. pp. 698-705.

Anna Waslewska et al: "Vascular endothelial growth factor in children with nephrotic syndrome treated with cyclosporine A", Acta Paediatrica. vol. 95. No. 3. Mar. 1, 2006. pp. 291-296.

Kitamoto et al. "Different response of urinary excretion of VEGF in patients with chronic and acute renal failure". Jan. 1, 2001. pp. 385-386.

Peterson, P.A. et al. "Differentiation of glomerular, tubular, and normal proteinuria : determinations of urinary excretion of$\beta$2-microglobulin, albumin, and total protein". The Journal of Clinical Investigation. 1969. vol. 48, No. 7, pp. 1189-1198.

Armbrecht HJ et al "Expressions of Calbindin-D Decreases with Age in Intestine and Kidney" Endocrinology 125:2950-2956 (1989).

Borke James L et al "Plasma membrane calcium pump and 28-kDa calcium binding protein in cells of rat kidney distal tubules" Am J Physiol 257 (Renal Fluid Electrolyte Physiol 26):F842-F849 (1989).

Bradley Andrew P "The Use of the Area Under the ROC Curve in the Evaluation of Machine Learning Algorithms" Pattern Recognition 30(7):1145-1159 (1997).

Bundgaard Jens R et al "Molecular Cloning and Expression of a cDNA Encoding NGAL: A Lipocalin Expressed in Human Neutrophils" Biochem Biophys Res Comm 202(3):1468-1475 (1994).

Cowland Jack B et al "Molecular Characterization and Pattern of Tissue Expression of the Gene for Neutrophil Gelatinase-Associated Lipocalin from Humans" Genomics 45:17-23 (1997).

Deng J-T et al "Decreased Renal Epidermal Growth Factor Expression in Cyclosporine-Treated Rats" Transplant Proc 26(5):2842-2844 (1994).

Di Paolo Salvatore et al "Renal expression and urinary concentration of EGF and IL-6 in acutely dysfunctioning kidney transplanted patients" Nephrol Dial Transplant 12:2687-2693 (1997).

Grenet Olivier et al "The Cyclosporine A-Induced Decrease in Rat Renal Calbindin-D28kDa Protein as a Consequence of a Decrease in its mRNA" Biochem Pharmacol 55:1131-1133 (1998).

Grenet Olivier et al "Evidence for the Impairment of the Vitamin D Activation Pathway by Cyclosporine A" Biochem Pharmacol 59:267-272 (2000).

Ichimura Takaharu et al "Kidney Injury Molecule-1 (KIM-1), a Putative Epithelial Cell Adhesion Molecule Containing a Novel Immunoglobulin Domain, is Up-regulated in Renal Cells after Injury" J Biological Chem 273(7):4135-4142 (1998).

Jenne Dieter E et al "Clusterin: the intriguing guises of a widely expressed glycoprotein" TIBS 17(4):154-159 (1992).

Kohri Kenjiro et al "Molecular Cloning and Sequencing of cDNA Encoding Urinary Stone Protein, Which is Identical to Osteopontin" Biochem Biophys Res Comm 184(2)859-864 (1992).

Kohri Kenjiro et al "Structure and Expression of the mRNA Encoding Urinary Stone Protein (Osteopontin)" J Biological Chem 268(20):15180-15184 (1993).

Komatsuda Atsushi "Analysis of Mutations in Alpha-Actinin 4 and Podocin Genes of Patients with Chronic Renal Failure Due to Sporadic Focal Segmental Glomerulosclerosis" Renal Failure 25(1):87-93 (2003).

Morin Nathalie J et al "Epidermal growth factor accelerates renal tissue repair in a model of gentamicin nephrotoxicity in rats" Am J Physiol 263 (Renal Fluid Electrolyte Physiol 32):F806-F811 (1992).

Persy Veerle P et al "Differences in osteopontin up-regulation between proximal and distal tubules after renal ischemia/reperfusion" Kidney Int 56:601-611 (1999).

Price Peter M et al "Regulation of transcription by the rate EGF gene promoter in normal and ischemic murine kidney cells" Am J Physiol 268 (Renal Fluid Electrolyte Physiol 37):F664-F670 (1995).

Rhoten William B et al "Cellular Gene Expression for Calbindin-D28k in Mouse Kidney" Anatomical Record 227:145-151 (1990).

Silkensen John R et al "Temporal Induction of Clusterin in Cisplatin Nephrotoxicity" J Am Soc Nephrol 8:302-305 (1997).

Yang Chul Woo et al "Influence of the renin-angiotensin system on epidermal growth factor expression in normal and cyclosporine-treated rat kidney" Kidney Int 60:847-857 (2001).

Zerega Barbara et al "Expression of NRL/NGAL (neu-related lipocalin/neutrophil gelatinase-associated lipocalin) during mammalian embryonic development and in inflammation" Euro J Cell Biol 79:165-172 (2000).

\* cited by examiner

Nephrotoxicants

| Compound | Tubul. | Glom. | Coll. D. | Mode of Toxicity |
|---|---|---|---|---|
| Gentamycin | x | | | Lysosomal phospholipidosis |
| Puromycin | x ($2^{nd}$) | x | | Damage to podocytes |
| Vancomycin | x | x | | Oxidative stress (free radicals) |
| Doxorubicin | x ($2^{nd}$) | x | | Oxidative stress to glom. filtr. membrane |
| Furosemide | x | | | Mineralization |
| Lithium carbonate | x | (x) | (x) | Influences formation of intracellular cyclic adenosine monophosphate |
| Cisplatin | x | (x) | (x) | Direct DNA alkylation of DNA, Ox. stress |
| FK506 | x | (x) | | Complex (vasoconstrict., calcification...) |

Hepatotoxicants

| | |
|---|---|
| α-Naphthyisothiocyanate (ANIT) | Cholangitis |
| Methapyrilene | Hepatocarcinogen (upon chronic treatment) |

FIG. 1

**COMPOUNDS ADMINISTERED IN THE *IN VIVO* STUDIES**

NUMBER OF KIDNEY LESIONS REPORTED IN ALL 10 STUDIES

| Primary Histopathology Process | Secondary Lesion | Structural Element / Segment | Nephrotoxicants | | | | | | Controls | | | | | | All | | | | | |
|---|---|---|---|---|---|---|---|---|---|---|---|---|---|---|---|---|---|---|---|---|
| | | | 0 | 1 | 2 | 3 | 4 | 5 | 0 | 1 | 2 | 3 | 4 | 5 | 0 | 1 | 2 | 3 | 4 | 5 |
| Tubular Cell Degeneration/Necrosis/Apoptosis | Necrosis | No precise localization possible | 412 | 19 | 14 | 2 | 0 | 0 | 291 | 1 | 0 | 0 | 0 | 0 | 703 | 20 | 14 | 2 | 0 | 0 |
| | | Prox. convoluted tubule (PCT, s1-s2) | 396 | 41 | 10 | 0 | 0 | 0 | 292 | 0 | 0 | 0 | 0 | 0 | 688 | 41 | 10 | 0 | 0 | 0 |
| | | Thick descending tubule (s3) | 347 | 81 | 17 | 2 | 0 | 0 | 292 | 0 | 0 | 0 | 0 | 0 | 639 | 81 | 17 | 2 | 0 | 0 |
| | | Thick ascending tubule | 406 | 36 | 5 | 0 | 0 | 0 | 292 | 0 | 0 | 0 | 0 | 0 | 698 | 36 | 5 | 0 | 0 | 0 |
| | | Distal convoluted tubule | 445 | 2 | 0 | 0 | 0 | 0 | 292 | 0 | 0 | 0 | 0 | 0 | 737 | 2 | 0 | 0 | 0 | 0 |
| | | Collecting duct | 429 | 17 | 1 | 0 | 0 | 0 | 292 | 0 | 0 | 0 | 0 | 0 | 721 | 17 | 1 | 0 | 0 | 0 |
| | Apoptosis | No precise localization possible | 443 | 4 | 0 | 0 | 0 | 0 | 290 | 2 | 0 | 0 | 0 | 0 | 733 | 6 | 0 | 0 | 0 | 0 |
| | | Prox. convoluted tubule (PCT, s1-s2) | 431 | 15 | 1 | 0 | 0 | 0 | 291 | 1 | 0 | 0 | 0 | 0 | 722 | 16 | 1 | 0 | 0 | 0 |
| | | Thick descending tubule (s3) | 443 | 3 | 1 | 0 | 0 | 0 | 291 | 1 | 0 | 0 | 0 | 0 | 734 | 4 | 1 | 0 | 0 | 0 |
| | | Thick ascending tubule | 446 | 1 | 0 | 0 | 0 | 0 | 292 | 0 | 0 | 0 | 0 | 0 | 738 | 1 | 0 | 0 | 0 | 0 |
| | | Collecting duct | 436 | 10 | 1 | 0 | 0 | 0 | 292 | 0 | 0 | 0 | 0 | 0 | 728 | 10 | 1 | 0 | 0 | 0 |
| Tubular Cell Regeneration | Basophilia | No precise localization possible | 373 | 54 | 11 | 9 | 0 | 0 | 258 | 34 | 0 | 0 | 0 | 0 | 631 | 88 | 11 | 9 | 0 | 0 |
| | | Prox. convoluted tubule (PCT, s1-s2) | 370 | 50 | 16 | 10 | | 1 | 0 | 283 | 8 | 1 | 0 | 0 | 0 | 653 | 58 | 17 | 10 | | 1 | 0 |
| | | Thick descending tubule (s3) | 352 | 46 | 8 | 21 | 7 | 0 | 0 | 290 | 1 | 1 | 0 | 0 | 0 | 642 | 47 | 8 | 21 | 7 | 0 | 0 |
| | | Thick ascending tubule | 373 | 50 | 15 | 9 | 0 | 0 | 290 | 2 | 0 | 0 | 0 | 0 | 663 | 52 | 15 | 9 | 0 | 0 |
| | | Distal convoluted tubule | 431 | 13 | 3 | 0 | 0 | 0 | 290 | 2 | 0 | 0 | 0 | 0 | 721 | 15 | 3 | 0 | 0 | 0 |
| | | Collecting duct | 420 | 22 | 5 | 0 | 0 | 0 | 291 | 0 | 1 | 0 | 0 | 0 | 711 | 22 | 6 | 0 | 0 | 0 |
| | Mitosis increase | No precise localization possible | 445 | 2 | 0 | 0 | 0 | 0 | 292 | 0 | 0 | 0 | 0 | 0 | 737 | 2 | 0 | 0 | 0 | 0 |
| | | Prox. convoluted tubule (PCT, s1-s2) | 419 | 26 | 2 | 0 | 0 | 0 | 292 | 0 | 0 | 0 | 0 | 0 | 711 | 26 | 2 | 0 | 0 | 0 |
| | | Thick descending tubule (s3) | 413 | 33 | 1 | 0 | 0 | 0 | 292 | 0 | 0 | 0 | 0 | 0 | 705 | 33 | 1 | 0 | 0 | 0 |
| | | Thick ascending tubule | 434 | 13 | 0 | 0 | 0 | 0 | 292 | 0 | 0 | 0 | 0 | 0 | 726 | 13 | 0 | 0 | 0 | 0 |
| | | Distal convoluted tubule | 441 | 3 | 3 | 0 | 0 | 0 | 292 | 0 | 0 | 0 | 0 | 0 | 733 | 3 | 3 | 0 | 0 | 0 |
| Tubular Cell Alterations | Hyaline droplet formation | No precise localization possible | 446 | 1 | 0 | 0 | 0 | 0 | 292 | 0 | 0 | 0 | 0 | 0 | 738 | 1 | 0 | 0 | 0 | 0 |
| | | Prox. convoluted tubule (PCT, s1-s2) | 399 | 36 | 11 | 1 | 0 | 0 | 283 | 7 | 2 | 0 | 0 | 0 | 682 | 43 | 13 | 1 | 0 | 0 |
| | | Thick descending tubule (s3) | 424 | 18 | 5 | 0 | 0 | 0 | 292 | 0 | 0 | 0 | 0 | 0 | 716 | 18 | 5 | 0 | 0 | 0 |
| | | Thick ascending tubule | 436 | 11 | 0 | 0 | 0 | 0 | 292 | 0 | 0 | 0 | 0 | 0 | 728 | 11 | 0 | 0 | 0 | 0 |
| | Hypertrophy/Enlargement | No precise localization possible | 439 | 8 | 0 | 0 | 0 | 0 | 292 | 0 | 0 | 0 | 0 | 0 | 731 | 8 | 0 | 0 | 0 | 0 |
| | | Prox. convoluted tubule (PCT, s1-s2) | 415 | 18 | 5 | 9 | 0 | 0 | 292 | 0 | 0 | 0 | 0 | 0 | 707 | 18 | 5 | 9 | 0 | 0 |
| | | Thick descending tubule (s3) | 411 | 22 | 12 | 2 | 0 | 0 | 292 | 0 | 0 | 0 | 0 | 0 | 703 | 22 | 12 | 2 | 0 | 0 |
| | | Loop of Henle | 446 | 1 | 0 | 0 | 0 | 0 | 292 | 0 | 0 | 0 | 0 | 0 | 738 | 1 | 0 | 0 | 0 | 0 |
| | | Thick ascending tubule | 437 | 10 | 0 | 0 | 0 | 0 | 292 | 0 | 0 | 0 | 0 | 0 | 729 | 10 | 0 | 0 | 0 | 0 |
| | | Distal convoluted tubule | 445 | 2 | 0 | 0 | 0 | 0 | 292 | 0 | 0 | 0 | 0 | 0 | 737 | 2 | 0 | 0 | 0 | 0 |
| | | Collecting duct | 417 | 20 | 9 | 1 | 0 | 0 | 292 | 0 | 0 | 0 | 0 | 0 | 709 | 20 | 9 | 1 | 0 | 0 |
| | Cellular sloughing | No precise localization possible | 428 | 16 | 3 | 0 | 0 | 0 | 292 | 0 | 0 | 0 | 0 | 0 | 720 | 16 | 3 | 0 | 0 | 0 |
| | | Prox. convoluted tubule (PCT, s1-s2) | 425 | 22 | 0 | 0 | 0 | 0 | 292 | 0 | 0 | 0 | 0 | 0 | 717 | 22 | 0 | 0 | 0 | 0 |
| | | Thick descending tubule (s3) | 416 | 26 | 5 | 0 | 0 | 0 | 292 | 0 | 0 | 0 | 0 | 0 | 708 | 26 | 5 | 0 | 0 | 0 |
| | | Thick ascending tubule | 443 | 2 | 2 | 0 | 0 | 0 | 292 | 0 | 0 | 0 | 0 | 0 | 735 | 2 | 2 | 0 | 0 | 0 |
| | | Distal convoluted tubule | 446 | 1 | 0 | 0 | 0 | 0 | 292 | 0 | 0 | 0 | 0 | 0 | 738 | 1 | 0 | 0 | 0 | 0 |
| | Vacuolation | Prox. convoluted tubule (PCT, s1-s2) | 417 | 27 | 3 | 0 | 0 | 0 | 289 | 3 | 0 | 0 | 0 | 0 | 706 | 30 | 3 | 0 | 0 | 0 |
| | | Thick descending tubule (s3) | 439 | 7 | 1 | 0 | 0 | 0 | 292 | 0 | 0 | 0 | 0 | 0 | 731 | 7 | 1 | 0 | 0 | 0 |
| | | Thick ascending tubule | 445 | 2 | 0 | 0 | 0 | 0 | 292 | 0 | 0 | 0 | 0 | 0 | 737 | 2 | 0 | 0 | 0 | 0 |
| | | Collecting duct | 440 | 6 | 1 | 0 | 0 | 0 | 292 | 0 | 0 | 0 | 0 | 0 | 732 | 6 | 1 | 0 | 0 | 0 |
| | Granular | Thick descending tubule (s3) | 443 | 4 | 0 | 0 | 0 | 0 | 292 | 0 | 0 | 0 | 0 | 0 | 735 | 4 | 0 | 0 | 0 | 0 |
| Intratubular Casts | Hyaline (proteinaceous, pigmented) | No precise localization possible | 407 | 34 | 6 | 0 | 0 | 0 | 290 | 2 | 0 | 0 | 0 | 0 | 697 | 36 | 6 | 0 | 0 | 0 |
| | | Prox. convoluted tubule (PCT, s1-s2) | 412 | 14 | 18 | 3 | 0 | 0 | 291 | 1 | 0 | 0 | 0 | 0 | 703 | 15 | 18 | 3 | 0 | 0 |
| | | Thick descending tubule (s3) | 413 | 9 | 13 | 12 | 0 | 0 | 291 | 1 | 0 | 0 | 0 | 0 | 704 | 10 | 13 | 12 | 0 | 0 |
| | | Loop of Henle | 401 | 30 | 12 | 4 | 0 | 0 | 292 | 0 | 0 | 0 | 0 | 0 | 693 | 30 | 12 | 4 | 0 | 0 |
| | | Thick ascending tubule | 394 | 33 | 15 | 5 | 0 | 0 | 292 | 0 | 0 | 0 | 0 | 0 | 686 | 33 | 15 | 5 | 0 | 0 |
| | | Distal convoluted tubule | 431 | 9 | 7 | 0 | 0 | 0 | 292 | 0 | 0 | 0 | 0 | 0 | 723 | 9 | 7 | 0 | 0 | 0 |
| | | Collecting duct | 429 | 16 | 2 | 0 | 0 | 0 | 291 | 1 | 0 | 0 | 0 | 0 | 720 | 17 | 2 | 0 | 0 | 0 |
| | Leukocytic | No precise localization possible | 435 | 12 | 0 | 0 | 0 | 0 | 292 | 0 | 0 | 0 | 0 | 0 | 727 | 12 | 0 | 0 | 0 | 0 |
| | | Thick descending tubule (s3) | 446 | 1 | 0 | 0 | 0 | 0 | 292 | 0 | 0 | 0 | 0 | 0 | 738 | 1 | 0 | 0 | 0 | 0 |
| | Mineralization | Thick descending tubule (s3) | 427 | 13 | 7 | 0 | 0 | 0 | 292 | 0 | 0 | 0 | 0 | 0 | 719 | 13 | 7 | 0 | 0 | 0 |
| | | Loop of Henle | 445 | 2 | 0 | 0 | 0 | 0 | 292 | 0 | 0 | 0 | 0 | 0 | 737 | 2 | 0 | 0 | 0 | 0 |
| | | Thick ascending tubule | 437 | 6 | 4 | 0 | 0 | 0 | 292 | 0 | 0 | 0 | 0 | 0 | 729 | 6 | 4 | 0 | 0 | 0 |
| Tubular Dilatation | Tubular Dilatation | Cortex | 371 | 19 | 39 | 18 | | 0 | 0 | 288 | 1 | 3 | 0 | 0 | 0 | 659 | 20 | 42 | 18 | | 0 | 0 |
| | | Medulla | 372 | 18 | 17 | 9 | 1 | 0 | 288 | 0 | 4 | 0 | 0 | 0 | 660 | 18 | 51 | 9 | 1 | 0 |
| | | Papilla | 426 | 17 | 4 | 0 | 0 | 0 | 292 | 0 | 0 | 0 | 0 | 0 | 718 | 17 | 4 | 0 | 0 | 0 |
| | Tubular Cystic Dilatation / Tubular Cyst(s) | Cortex | 446 | 0 | 0 | 1 | 0 | 0 | 292 | 0 | 0 | 0 | 0 | 0 | 738 | 0 | 0 | 1 | 0 | 0 |
| | | Medulla | 445 | 1 | 0 | 1 | 0 | 0 | 291 | 1 | 0 | 0 | 0 | 0 | 736 | 2 | 0 | 1 | 0 | 0 |
| Glomerular Alteration | Mesangial proliferation/expan | Glomerulus | 407 | 33 | 7 | 0 | 0 | 0 | 292 | 0 | 0 | 0 | 0 | 0 | 699 | 33 | 7 | 0 | 0 | 0 |
| | Glomerular Vacuolation | Glomerulus | 433 | 13 | 1 | 0 | 0 | 0 | 292 | 0 | 0 | 0 | 0 | 0 | 725 | 13 | 1 | 0 | 0 | 0 |
| Juxtaglomerular Apparatus Hypertrophy | | Juxtaglomerular | 417 | 18 | 12 | 0 | 0 | 0 | 292 | 0 | 0 | 0 | 0 | 0 | 709 | 18 | 12 | 0 | 0 | 0 |
| Pelvis Dilatation | | Pelvis | 435 | 7 | 4 | 1 | 0 | 0 | 278 | 11 | 3 | 0 | 0 | 0 | 713 | 18 | 7 | 1 | 0 | 0 |
| Inflammation | Interstitial, acute | Pelvis | 447 | 0 | 0 | 0 | 0 | 0 | 291 | 1 | 0 | 0 | 0 | 0 | 738 | 1 | 0 | 0 | 0 | 0 |
| | Interstitial, chronic | Cortex | 391 | 56 | 0 | 0 | 0 | 0 | 270 | 20 | 2 | 0 | 0 | 0 | 661 | 76 | 2 | 0 | 0 | 0 |
| | | Medulla | 438 | 9 | 0 | 0 | 0 | 0 | 292 | 0 | 0 | 0 | 0 | 0 | 730 | 9 | 0 | 0 | 0 | 0 |
| | | Pelvis | 447 | 0 | 0 | 0 | 0 | 0 | 291 | 1 | 0 | 0 | 0 | 0 | 738 | 1 | 0 | 0 | 0 | 0 |
| Fibrosis | Interstitial | Cortex | 444 | 3 | 0 | 0 | 0 | 0 | 291 | 1 | 0 | 0 | 0 | 0 | 735 | 4 | 0 | 0 | 0 | 0 |
| | | Medulla | 447 | 0 | 0 | 0 | 0 | 0 | 290 | 2 | 0 | 0 | 0 | 0 | 737 | 2 | 0 | 0 | 0 | 0 |
| | Interstitial Bowman's capsule | Glomerulus | 433 | 14 | 0 | 0 | 0 | 0 | 291 | 1 | 0 | 0 | 0 | 0 | 724 | 15 | 0 | 0 | 0 | 0 |
| Concentric Lamellar Bodies | | Cortex | 439 | 8 | 0 | 0 | 0 | 0 | 290 | 2 | 0 | 0 | 0 | 0 | 729 | 10 | 0 | 0 | 0 | 0 |
| | | Medulla | 447 | 0 | 0 | 0 | 0 | 0 | 291 | 1 | 0 | 0 | 0 | 0 | 738 | 1 | 0 | 0 | 0 | 0 |
| | | Papilla | 446 | 1 | 0 | 0 | 0 | 0 | 292 | 0 | 0 | 0 | 0 | 0 | 738 | 1 | 0 | 0 | 0 | 0 |
| Urothelial hypertrophy-hyperplasia | | Papilla | 446 | 1 | 0 | 0 | 0 | 0 | 292 | 0 | 0 | 0 | 0 | 0 | 738 | 1 | 0 | 0 | 0 | 0 |

FIG. 3

HISTOPATHOLOGY KIDNEY LESIONS

FIG. 4

RENAL HISTOPATHOLOGY MATRIX FOR THE CISPLATIN STUDY

| Histopathology Finding | Count |
|---|---|
| acute coagulative necrosis | 9 |
| acute hepatocellular necrosis | 1 |
| apoptosis / single cell necrosis | 13 |
| bile duct degeneration / necrosis | 19 |
| bile duct hyperplasia | 67 |
| bile duct proliferation | 2 |
| biliary epithelial mitotic figures | 5 |
| capsular fibrosis / focal | 2 |
| capsular inflammation | 1 |
| capsular thickening | 1 |
| centrilobular hepatocellular atrophy | 2 |
| coagulative necrosis | 1 |
| congestion | 4 |
| extramedullary hematopoiesis | 8 |
| focal necrosis | 55 |
| glycogen content | 112 |
| glycogen depletion | 31 |
| granuloma(s) | 9 |
| hemorrhage | 1 |
| hepatocellular atrophy | 7 |
| hepatocellular hemosiderosis | 7 |
| hepatocellular hemosiderosis / focal | 1 |
| hepatocellular hemosiderosis / left papillary process | 2 |
| hepatocellular microvacuolation | 2 |
| hepatocellular vacuolation | 10 |
| increased mitotic figures | 41 |
| inflammation / necrosis | 22 |
| inflammation / necrosis / focal | 4 |
| mononuclear cell aggregation | 88 |
| periportal hepatocellular vacuolation | 27 |
| periportal inflammatory cell infiltration | 18 |
| perivascular inflammation | 1 |
| pigmented-laden macrophages | 6 |
| pigment-laden macrophages | 1 |
| portal edema | 3 |
| portal fibrosis | 10 |
| portal granulocyte infiltration | 29 |
| portal mononuclear cell infiltration | 107 |
| prominent bile duct nuclei | 3 |
| prominent hepatocellular nucleoli | 54 |
| prominent Kupffer cell | 1 |
| single cell necrosis | 53 |
| sinusoidal ectesia | 1 |
| subcapsular fibrosis | 1 |
| subcapsular necrosis | 1 |

FIG. 5

HISTOPATHOLOGY LIVER LESIONS

| Biomarker | Entitiy | Matrix | Pathology | AUC | Direct | N° Ctrls | N° Dis | Thr | Spec % | Sens % |
|---|---|---|---|---|---|---|---|---|---|---|
| Kim1 | Protein | Urine | Proximal Tubular Damage | 0.91 ± 0.02 | + | 283 | 132 | 1.87 | 95 | 79 |
| Clusterin | Protein | Urine | Proximal Tubular Damage | 0.88 ± 0.02 | + | 289 | 132 | 1.85 | 95 | 70 |
| LCN2 | Protein | Urine | Proximal Tubular Damage | 0.75 ± 0.03 | + | 289 | 132 | 2.50 | 95 | 52 |
| SPP1 | Protein | Urine | Proximal Tubular Damage | 0.71 ± 0.03 | + | 289 | 132 | 2.39 | 95 | 34 |
| Timp1 | Protein | Urine | Proximal Tubular Damage | 0.73 ± 0.03 | + | 289 | 132 | 2.98 | 95 | 34 |
| Calb1 | Protein | Urine | Collecting Duct Damage / Regeneration | 0.87 ± 0.03 | + | 291 | 52 | 1.93 | 95 | 48 |
| Calb1 | Protein | Urine | Juxtaglomerular Apparatus Hypertrophy | 0.98 ± 0.02 | - | 292 | 30 | 0.35 | 95 | 87 |
| B2-Microglob | Protein | Urine | Glomerular Alterations / Damage | 0.89 ± 0.03 | + | 291 | 40 | 2.50 | 95 | 78 |
| Total Protein | Protein | Urine | Glomerular Alterations / Damage | 0.86 ± 0.04 | + | 291 | 40 | 1.50 | 95 | 78 |
| Cystatin C | Protein | Urine | Glomerular Alterations / Damage | 0.91 ± 0.03 | + | 291 | 40 | 2.00 | 95 | 80 |
| NAG | Protein | Urine | Tubular Damage / Regeneration / Dilatation | 0.79 ± 0.02 | + | 244 | 215 | 1.38 | 95 | 45 |
| LDH | Protein | Urine | Tubular Damage / Regeneration / Dilatation | 0.73 ± 0.02 | + | 244 | 215 | 2.10 | 95 | 38 |
| Calcium | Protein | Urine | Tubular Mineralization | 0.99 ± 0.01 | + | 292 | 20 | 1.59 | 95 | 100 |
| Kim1 | Protein | Blood | Proximal Tubular Damage | 0.74 ± 0.03 | + | 266 | 119 | 2.27 | 95 | 13 |
| LCN2 | Protein | Blood | Proximal Tubular Damage | 0.72 ± 0.03 | + | 289 | 132 | 2.54 | 95 | 31 |
| SPP1 | Protein | Blood | Intratubular Hayline Casts (proteinaceous, pigmented) | 0.84 ± 0.03 | + | 290 | 82 | 1.24 | 95 | 63 |
| SPP1 | Protein | Blood | Thick Ascending Tubular Damage / Regeneration | 0.83 ± 0.03 | + | 290 | 84 | 1.24 | 95 | 61 |
| Cystatin C | Protein | Blood | Glomerular Alterations / Damage or Tubular Damage/ Regeneration / Dilatation | 0.81 ± 0.02 | + | 244 | 224 | 1.22 | 95 | 54 |
| Cystatin C | Protein | Blood | Proximal Tubular Damage | 0.89 ± 0.02 | + | 289 | 132 | 1.23 | 95 | 64 |
| Cystatin C | Protein | Blood | Glomerular Alterations / Damage | 0.89 ± 0.03 | + | 291 | 40 | 1.23 | 95 | 75 |
| B2-Microglob | Protein | Blood | Proximal Tubular Damage | 0.81 ± 0.02 | + | 289 | 132 | 1.62 | 95 | 39 |
| Total Protein | Protein | Blood | Glomerular Alterations / Damage | 0.99 ± 0.01 | - | 291 | 40 | 0.93 | 95 | 95 |
| Albumin | Protein | Blood | Glomerular Alterations / Damage | 0.98 ± 0.02 | - | 291 | 40 | 0.91 | 95 | 88 |
| ALP | Protein | Blood | Glomerular Alterations / Damage | 0.95 ± 0.02 | - | 291 | 40 | 0.71 | 95 | 73 |
| Natrium | Ion | Blood | Distal Tubular Damage / Regeneration | 0.88 ± 0.05 | - | 290 | 22 | 0.98 | 95 | 64 |
| Natrium | Ion | Blood | Tubular Mineralization | 0.95 ± 0.04 | - | 292 | 20 | 0.98 | 95 | 75 |
| Kim1 | mRNA | Kidney | Proximal Tubular Damage | 0.99 ± 0.01 | + | 289 | 132 | 3.34 | 95 | 98 |
| Clusterin | mRNA | Kidney | Proximal Tubular Damage | 0.93 ± 0.02 | + | 281 | 132 | 1.52 | 95 | 77 |
| SPP1 | mRNA | Kidney | Proximal Tubular Damage | 0.93 ± 0.02 | + | 289 | 132 | 2.66 | 95 | 78 |
| Timp1 | mRNA | Kidney | Proximal Tubular Damage | 0.91 ± 0.02 | + | 289 | 132 | 1.84 | 95 | 75 |
| LCN2 | mRNA | Kidney | Proximal Tubular Damage | 0.87 ± 0.02 | + | 289 | 132 | 4.10 | 95 | 70 |
| VEGF | mRNA | Kidney | Proximal Tubular Damage | 0.82 ± 0.02 | - | 289 | 132 | 0.85 | 95 | 58 |
| EGF | mRNA | Kidney | Proximal Tubular Damage | 0.88 ± 0.02 | - | 289 | 132 | 0.80 | 95 | 70 |
| CYR61 | mRNA | Kidney | Tubular Damage / Regeneration / Dilatation | 0.79 ± 0.02 | + | 244 | 215 | 1.82 | 95 | 52 |
| Calb1 | mRNA | Kidney | Juxtaglomerular Apparatus Hypertrophy | 1.00 ± 0.00 | - | 292 | 30 | 0.62 | 95 | 100 |
| Cystatin C | mRNA | Kidney | Glomerular Alterations / Damage | 0.94 ± 0.03 | + | 291 | 40 | 1.29 | 95 | 75 |
| KIM1 | mRNA | Kidney | Tubular Damage / Regeneration / Dilatation | 0.87 ± 0.02 | + | 244 | 215 | 2.90 | 95 | 78 |
| Clusterin | mRNA | Kidney | Tubular Damage / Regeneration / Dilatation | 0.82 ± 0.02 | + | 244 | 215 | 1.45 | 95 | 59 |
| EGF | mRNA | Kidney | Tubular Damage / Regeneration / Dilatation | 0.83 ± 0.02 | - | 244 | 215 | 0.80 | 95 | 59 |
| Creatinine | Molecule | Blood | Proximal Tubular Damage | 0.73 ± 0.03 | + | 289 | 132 | 1.15 | 95 | 40 |
| Creatinine | Molecule | Blood | Glomerular Alterations / Damage | 0.53 ± 0.05 | - | 291 | 40 | 0.95 | 95 | 33 |
| Creatinine | Molecule | Blood | Tubular Damage / Regeneration / Dilatation | 0.70 ± 0.02 | + | 244 | 215 | 1.15 | 95 | 31 |
| Creatinine | Molecule | Blood | Glomerular Alterations / Damage or Tubular Damage/ Regeneration / Dilatation | 0.71 ± 0.02 | + | 244 | 224 | 1.15 | 95 | 30 |
| Creatinine | Molecule | Blood | Collecting Duct Damage / Regeneration | 0.85 ± 0.03 | + | 291 | 52 | 1.15 | 95 | 52 |
| Creatinine | Molecule | Blood | Distal Tubular Damage / Regeneration | 0.83 ± 0.05 | + | 290 | 22 | 1.15 | 95 | 50 |
| Creatinine | Molecule | Blood | Thick Ascending Tubular Damage / Regeneration | 0.77 ± 0.03 | + | 290 | 84 | 1.15 | 95 | 43 |
| Creatinine | Molecule | Blood | Juxtaglomerular Apparatus Hypertrophy | 0.75 ± 0.05 | + | 292 | 30 | 1.15 | 95 | 13 |
| Creatinine | Molecule | Blood | Tubular Mineralization | 0.90 ± 0.05 | + | 292 | 20 | 1.15 | 95 | 30 |
| Creatinine | Molecule | Blood | Intratubular Hayline Casts (proteinaceous, pigmented) | 0.67 ± 0.04 | + | 290 | 82 | 1.15 | 95 | 43 |
| BUN | Molecule | Blood | Proximal Tubular Damage | 0.79 ± 0.03 | + | 289 | 132 | 1.20 | 95 | 51 |
| BUN | Molecule | Blood | Glomerular Alterations / Damage | 0.80 ± 0.04 | + | 291 | 40 | 1.20 | 95 | 55 |
| BUN | Molecule | Blood | Tubular Damage / Regeneration / Dilatation | 0.70 ± 0.02 | + | 244 | 215 | 1.20 | 95 | 40 |
| BUN | Molecule | Blood | Glomerular Alterations / Damage or Tubular Damage/ Regeneration / Dilatation | 0.70 ± 0.02 | + | 244 | 224 | 1.20 | 95 | 39 |
| BUN | Molecule | Blood | Collecting Duct Damage / Regeneration | 0.58 ± 0.04 | + | 291 | 52 | 1.20 | 95 | 38 |
| BUN | Molecule | Blood | Distal Tubular Damage / Regeneration | 0.73 ± 0.06 | + | 290 | 22 | 1.20 | 95 | 41 |
| BUN | Molecule | Blood | Thick Ascending Tubular Damage / Regeneration | 0.86 ± 0.03 | + | 290 | 84 | 1.20 | 95 | 60 |
| BUN | Molecule | Blood | Juxtaglomerular Apparatus Hypertrophy | 0.62 ± 0.06 | + | 292 | 30 | 1.20 | 95 | 10 |
| BUN | Molecule | Blood | Tubular Mineralization | 0.84 ± 0.06 | + | 292 | 20 | 1.20 | 95 | 45 |
| BUN | Molecule | Blood | Intratubular Hayline Casts (proteinaceous, pigmented) | 0.80 ± 0.03 | + | 290 | 82 | 1.20 | 95 | 55 |

FIG. 6

RESULTS OF THE ROC ANALYSIS FOR BIOMARKERS

HEPTATOXICITY BY DIFFERENT PROTEIN BIOMARKERS

HEPTATOXICITY BY DIFFERENT PROTEIN BIOMARKERS

KIDNEY INJURY BY DIFFERENT PROTEIN BIOMARKERS AND CLINICAL CHEMISTRY PARAMETERS

KIDNEY INJURY BY DIFFERENT PROTEIN BIOMARKERS AND
CLINICAL CHEMISTRY PARAMETERS

KIDNEY INJURY BY DIFFERENT PROTEIN BIOMARKERS AND CLINICAL CHEMISTRY PARAMETERS

KIDNEY INJURY BY TRANSCRIPTION OF DIFFERENT GENES -

ASSAY OF mRNA FROM KIDNEY

KIDNEY INJURY BY TRANSCRIPTION OF DIFFERENT GENES - ASSAY OF mRNA FROM KIDNEY

USE OF β-2-MICROGLOBULIN TO ASSESS GLOMERULAR ALTERATIONS AND DAMAGE IN THE KIDNEY

This application is a 371 of PCT/EP2008/053504 filed on Mar. 25, 2008, which claims benefit of U.S. Provisional Application No. 60/908,094 filed on Mar. 26, 2007, which in their entirety are herein incorporated by reference.

FIELD OF THE INVENTION

The invention relates to biomarker signatures and their use in methods and devices for the monitoring, prognosis, diagnosis, and/or treatment of kidney or liver toxicity, and more specifically renal tubular toxicity as a consequence of disease or drug treatment.

BACKGROUND OF THE INVENTION

Progression to end-stage renal failure is the final common pathway of various proteinuric nephropathies. The degree of proteinuria is associated with the rate of progression of renal disease.

In human proteinuric diseases, tubulointerstitial injury is a better predictor of renal function decline than is glomerular damage. Filtered tubulotoxic plasma proteins are believed to be responsible for this association, although the nature of these proteins is uncertain. Filtered proteins partly exert their detrimental effects via activation of proximal tubular cells (PTC), which excrete chemokines and cytokines, resulting in inflammation, myotransformation of interstitial fibroblasts, fibrosis, and apoptosis. This ultimately leads to end-stage renal failure. Renal tubular epithelial cells are therefore considered to be crucial in the progression of interstitial damage. Proteinuria has been proposed to cause tubular injury and interstitial fibrosis.

There is a continuing need in the art for determining and monitoring the kidney and liver function in animals and man after drug treatment or when kidney function is impaired due to a disease.

SUMMARY OF THE INVENTION

The invention provides tests and devices to diagnose or predict the state, function and integrity of kidney and liver. The biomarkers of the invention, other clinical chemistry parameters or combinations thereof can be converted into an assay, test or device to diagnose the status of kidney or liver, to monitor adverse events such as drug-induced nephrotoxicity or hepatotoxicty, to adapt treatment regimens of drugs on the basis of the status of kidney or liver, or to develop a clinical test for the diagnosis of disease in kidney or liver or the prevalence of it.

The invention makes possible the prediction, classification, correlation and diagnosis of kidney or liver toxicity based on the data presented herein.

Also described herein are animal studies, in which different model nephrotoxicants and hepatotoxicants were administered to the animals using different dosing regimens. Different biological samples were sampled from the animals at different time points. Urine, blood, organ tissues, mRNA from organ tissues and blood were sampled at different time points and in different treatment groups. The animals were assessed during the in vivo period and afterwards using different methods, in particular using clinical observations, in vivo data (such as body weight, food consumption, macroscopic and microscopic examinations of organs (in particular, kidney and liver).

BRIEF DESCRIPTION OF THE DRAWINGS

The drawing figures depict preferred embodiments by way of example, not by way of limitations.

FIG. 1 is a list of the compounds administered to the animals in the in vivo studies.

FIG. 3 is a table showing the histopathology kidney lesions that were reported in the 10 in vivo studies. The number of occurrences are listed categorized by grade and by treatment groups (nephrotoxicant-treated versus vehicle- and hepatotoxicant-treated).

FIG. 4 is a renal histopathology matrix for the cisplatin study. Each column represents a localized lesion. Each row corresponds to an animal, whereby the animals are ordered by dose-group (controls, low-dosed, mid-dosed, and high-dosed) and within each dose-group by termination time-point. If a lesion was reported, the grade is represented by an orange box with the corresponding grade in it (grade 1, grade 2-5, no report/grade 0). Dominating processes are labeled.

FIG. 5 is a table showing the histopathology liver lesions that were reported in the 10 in vivo studies. The number of occurrences is listed.

FIG. 6 is a table showing the results of the receiver operator characteristic (ROC) analysis for biomarkers and current standards for certain pathologies. Column 1 represents the biomarker, column 2 the molecular entity, column three the medium, in which the biomarker was measured and column 4 the pathology for which the ROC analysis was performed. Column 5 represents the AUCs and the standard error thereof. Column 6 indicates if a biomarker value increases with the presence of the corresponding pathology (+) or decreases (−). Columns 7 and 8 display the numbers of animals used for the corresponding analyses. Column 11 shows the corresponding sensitivity for 95% specificity (column 10) and column 9 the corresponding threshold of the biomarker. Besides of the biomarkers of interest, also the results for the current standards BUN and serum creatinine are shown for the 10 pathologies of interest. This table demonstrates the use and performance of implementations of devices, assays, diagnostic test or diagnostic kits of the listed specific biomarkers to monitor the listed specific renal pathologies.

DETAILED DESCRIPTION OF THE INVENTION

Figure 2:
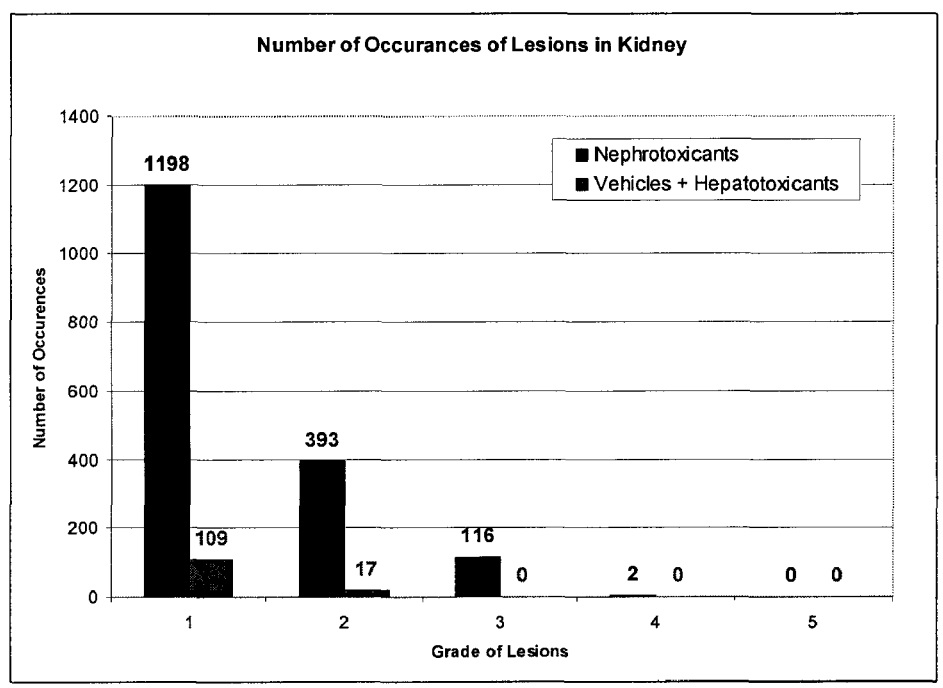
FIG. 2 shows the number of kidney lesions, which were reported in all 10 studies. The numbers are sub-divided by grade and by treatment groups (nephrotoxicant-treated animals versus vehicle- and hepatotoxicant-treated animals).

Definitions. As used herein the expression "renal toxicity" or "renal injury" or similarly "kidney disorder" shall all mean a renal or kidney failure or dysfunction either sudden (acute) or slowly declining over time (chronic), that may be triggered by a number of disease or; disorder processes, including (but not limited to) for acute renal toxicity: sepsis I (infection), shock, trauma, kidney stones, kidney infection, drug toxicity, poisons or toxins, or after injection with an iodinated contrast dye (adverse effect); and for chronic renal toxicity: long-standing hypertension, diabetes, congestive heart failure, lupus, or sickle cell anemia. Both forms of renal failure result in a life-threatening metabolic derangement.

The expression "body samples" shall include but is not limited to biopsies, preferably of the kidney, and body fluids such as blood, plasma, serum, lymph, cerebrospinal fluid, cystic fluid, ascites, urine, stool and bile. One advantage of the invention is that one marker can be particularly well monitored in body fluids, such as plasma or urine. For instance, level of expression of clusterin can be particularly well determined in plasma.

As used herein the term "individual" shall mean a human person, an animal, such as mouse or rat, or a population or pool of individuals.

As used herein, the term "candidate agent" or "drug candidate" can be natural or synthetic molecules such as proteins or fragments thereof, antibodies, small molecule inhibitors or agonists, nucleic acid molecules, organic and inorganic compounds and the like.

General methods. In practicing the invention, many conventional techniques in molecular biology, microbiology, and recombinant DNA are used. These techniques are well known and are explained in, for example, *Current Protocols in Molecular Biology, Volumes I, II, and III*, 1997 (F. M. Ausubel ed.); Sambrook et al., *Molecular Cloning: A Laboratory Manual, Second Edition* (Cold Spring Harbor Laboratory Press, Cold Spring Harbor, N.Y., 1989); *DNA Cloning: A Practical Approach, Volumes I and II*, D. N. Glover ed. (1985); *Oligonucleotide Synthesis*, M. L. Gait ed. (1984); Hames & Higgins, *Nucleic Acid Hybridization*, (1985); *Transcription and Translation*, Hames & Higgins eds. (1984); *Animal Cell Culture*, R. I. Freshney ed. (1986); *Immobilized Cells and Enzymes*, (IRL Press, 1986); Perbal, *A Practical Guide to Molecular Cloning*; the series, *Methods in Enzymology* (Academic Press, Inc., 1984); *Gene Transfer Vectors for Mammalian Cells*, J. H. Miller & M. P. Calos eds. (Cold Spring Harbor Laboratory, 1987); and *Methods in Enzymology* Vol. 154 and Vol. 155 (Wu & Grossman, and Wu, eds., respectively).

All references cited herein are incorporated herein by reference in their entirety and for all purposes to the same extent as if each individual publication or patent or patent application was specifically and individually indicated to be incorporated by reference in its entirety for all purposes. In addition, all GenBank accession numbers, Unigene Cluster numbers and protein accession numbers cited herein are incorporated herein by reference in their entirety and for all purposes to the same extent as if each such number was specifically and individually indicated to be incorporated by reference in its entirety for all purposes.

Biomarkers of the invention. The genomic and protein expressions of several biomarkers (listed in TABLES 1 and 2) in kidney tissues was measured. The course of the related protein in urine and plasma was also measured. A correlation of genomic or protein expression in tissue, urine and plasma concentration was made with histopathology and with urinalysis parameters such as proteinuria (TABLE 2) and plasma clinical chemistry parameters (see TABLE 2) such as creatinine, blood urea nitrogen (BUN) and creative clearance. The question that was investigated was whether urinary renal biomarkers reflect renal tissue damage and possibly kidney function.

TABLE 1 provides a list of biomarkers assessed on a transcription level (mRNA from kidney and liver) and on a protein level (in urine and blood). The measurements of these biomarkers in TABLE 1, described further below.

TABLE 1

List of Biomarkers Assessed on a Transcription Level and on a Protein Level

| Name | mRNA | Protein | Swissprot Nbr | Gene Symbol |
|---|---|---|---|---|
| β-2-microglobulin | no | yes | P07151 | B2m |
| N-acetyl-beta-glucosaminidase, Beta-hexosaminidase alpha chain, NAG | no | yes | Q641X3 | Hexa |
| Alpha Glutathione-S-transferase (alpha-GST)/ Glutathione S-transferase alpha 5 | yes | yes | P46418 | Gsta5 |
| Calbindin d28 | yes | yes | P07171 | Calb1 |

TABLE 1-continued

List of Biomarkers Assessed on a Transcription Level and on a Protein Level

| Name | mRNA | Protein | Swissprot Nbr | Gene Symbol |
|---|---|---|---|---|
| Clusterin | yes | yes | P05371 | Clu |
| Cystatin C | yes | yes | P14841 | Cst3 |
| Cysteine-rich protein-61 (CYR61) | yes | yes | Q9ES72 | Cyr61 |
| Epidermal growth factor (EGF) | yes | yes | P07522 | Egf |
| Glutathione S-transferase Mu 1, GST Yb1, mu GST | yes | yes | P04905 | Gstm1 |
| Kidney Injury Molecule-1, Hepatitis A virus cellular receptor 1 homolog, Kim-1 | yes | yes | O54947 | Havcr1 or Kim1 |
| Neutrophil gelatinase-associated lipocalin, HNL, Lipocalin 2 | yes | yes | P30152 | Lcn2 |
| Osteopontin, Secreted phosphoprotein 1 | yes | yes | P08721 | Spp1 or 2b7 |
| Podocin | yes | yes | Q8K4G9 | Nphs2 |
| Metalloproteinase inhibitor 1, TIMP-1 | yes | yes | P30120 | Timp1 |
| VEGF/Vascular endothelial growth factor A | yes | yes | P16612 | VEGF of VEGF-A |

Among the biomarkers of the invention are the following:

Calbindin D-28k is a calcium-binding protein member of the large EF-hand family. Calbindin D-28k is present in all classes of vertebrates and in a wide range of tissues. Several researchers have shown that in the kidney highest amounts of Calbindin D-28k are localized in the distal tubule, which correlates with the role of the distal tubule as the site of calcium absorption. Rhoten W B et al., *Anat. Rec.* 227:145-151; Borke J L et al., *Am. J. Physiol.* (*Renal Fluid Electrolyte Physiol*) 257: F842-F849 26 (1989). Furthermore, it has been shown that the decreased expression of calbindin D-28k with age may contribute to the age-related decrease in $Ca^{++}$ transport in intestine and kidney. Armbrecht H J et al., *Endocrinology* 125: 2950-2956 (1989). Cyclosporine A-induced decrease in rat renal calbindin-D 28k protein is a consequence of a decrease in its mRNA. Grenet O et al., *Biochem. Pharmacol.* 55(7): 1131-1133 (1998); Grenet O et al., *Biochem. Pharmacol.* 59(3): 267-272 (2000).

Clusterin, also known as testosterone-repressed prostate message 2 (TRPM-2) is an ubiquitous, secreted glycoprotein induced in many organs, including the kidney, at times of tissue injury and/or remodeling, and it has been found in the tubular lumen of epithelial ducts. Jenne D E & Tschopp J, *Trends Biochem. Sci.* 14: 154-159 (1992). Clusterin may preserve cell interactions that are otherwise perturbed by renal insults. Silkensen J R et al., *J. Am. Soc. Nephrol.* 8(2): 302-305 (1997). Furthermore, cyclosporine A (CsA) increases clusterin mRNA levels in the rat kidney. Darby I A et al., *Exp. Nephrol.* 3(4): 234-239 (1995).

Epidermal growth factor (EGF) is a small polypeptide belonging to a class of molecules that can mediate cell growth, differentiation, and acute phase responses. EGF mRNA is transcribed primarily in cells of the kidney. In a variety of experimentally induced forms of acute renal failure, the mRNA and protein levels for kidney EGF fall markedly and remain low for a prolonged period. Price P M et al., *Am J Physiol.* 268(4 Pt 2): F664-670 (1995). Furthermore, EGF is believed to play a major role in renal tubular regeneration after ischemic injury to the kidney (Di Paolo S, et al., *Nephrol Dial Transplant* 2: 2687-2693 (1997)) and in renal tissue repair after drug-induced nephrotoxicity (Morin N J et al., *Am. J. Physiol.* 263: F806-F811 (1992). EGF expression levels have been shown to be markedly reduced in renal transplantation patients suffering from chronic rejection or drug-induced nephrotoxicity. In addition, decreases in EGF expression in the kidney following cyclosporine A (CsA) treatment have been reported. Deng J T et al., *Transplant Proc.* 26(5): 2842-2844; Yang C W, et al., *Kindey Int.* 60: 847-857 (2001).

Kidney injury molecule-1 (Kim-1) is a type 1 membrane protein containing an extracellular, six-cysteine immunoglobulin domain. Kim-1 mRNA and protein are expressed at a low, almost undetectable, level in normal kidney but are increased dramatically in proximal tubules in the postischemic kidney Kim-1 is implicated in the restoration of the morphological integrity and function to post-ischemic kidneys. Ichimura T et al., *J. Biol. Chem.* 273: 4135-4142 (1998). Kim-1 is sometimes described as "Havcr1". The early and abundant tubular expression following different types of injury makes Kim-1 a specific marker of tubular cell injury that may be linked to recuperative or damaging mechanisms that directs the process of interstitial damage. See WO 2004/005544, incorporated herein by reference.

Alpha-2u globulin related-protein (Alpha-2u), also known as lipocalin 2 (LCN2) or neutrophil gelatinase-associated lipocalin (NGAL) in humans, is stored in granules of neutrophils. It binds to small lipophilic substances and is believed to have a role in inflammation. Bundgaard J R et al., *Biochem. Biophys. Res. Commun.* 202: 1468-1475 (1994); Cowland J B & Borregaard N, *Genomics* 45: 17-23 (1997); Zerega B et al., *Eur. J. Cell Biol.* 79, 165-172 (2000).

Osteopontin (OPN), also known as secreted phosphoprotein 1 (SPP1), is a secreted, highly acidic and glycosylated phosphoprotein containing an arginine-glycine-aspartic acid (RGD) cell adhesion motif. OPN up-regulation has been demonstrated in several models of renal injury, suggesting a possible role in tissue remodeling and repair. Persy V P et al., *Kidney Int.* 56(2): 601-611 (1999). Osteopontin was also found to be a major component of urinary calcium oxalate stones. Kohri K et al., *Biochem. Biophys. Res. Commun.* 84: 859-864 (1992). Furthermore, OPN is highly expressed in distal tubular cells in rats prone to urinary stone formation. Kohri K et al., *J. Biol. Chem.* 268: 15180-15184 (1993).

Podocin, also known as PDCN, SRN1, nephrosis 2, idiopathic, is a protein expressed in renal podocytes and plays a role in the regulation of glomerular permeability. It is almost exclusively expressed in the podocytes of fetal and mature kidney glomeruli. Mutations of podocyte proteins, e.g. podocin, result in congenital focal segmental glomerulosclerosis. Komatsuda A et al., *Ren. Fail.* 25(1): 87-93 (2003)) and is mainly implicated in steroid-resistant nephrotic syndrome.

Vascular Endothelial Growth Factor (VEGF) is known to promote angiogenesis, increase vascular permeability, serve as a chemotactic for monocytes, and has a role in diabetes, wound healing, inflammatory responses, and tissue remodeling. Benjamin L E, *Am J Pathol.* 158: 1181-1184 (2001).

As each marker can be linked to different renal pathological findings, it is possible to identify gene expression products of such markers that are particularly linked to a renal pathology. For instance, the calbindin-D28k level is used as an early marker for calcium disturbance predictor for mineralization. The Kim-1 level is a marker for general kidney insult. The OPN level is an early marker for macrophage infiltration often associated with kidney toxicity and a marker for tissue remodeling upon renal injury. The EGF level is an early marker for general kidney toxicity. The clusterin level is an early marker for immune-mediated kidney toxicity.

TABLE 2 provides a list of parameters from clinical chemistry determined in urine and in blood. The measurements of these biomarkers in TABLE 2, described further below.

TABLE 2

List of Parameters from Clinical Chemistry

| Urine Parameters | Blood Parameters |
| --- | --- |
| Calcium (Ca++) | Albumin (ALB) |
| Chloride (Cl−) | Albumin/globulin ratio (A/G) |
| Creatinine (CREAT) | Alkaline phosphatase (ALP) |
| Creatinine clearance (CLEAR) | Alanine Aminotransferase (ALAT) |
| Inorganic phosphorus (I. PHOS) | Aspartate Aminotransferase (ASAT) |
| Lactate dehydrogenase (LDH) | Calcium (Ca++) |
| Magnesium (Mg++) | Chloride (Cl−) |
| Potassium (K+) | Creatinine (CREAT) |
| Sodium (Na+) | Glucose (GLUC) |
| Specific gravity (SP. GRAV) | Inorganic phosphorus (I. PHOS) |
| Total proteins (PROT) | Lactate dehydrogenase (LDH) |
| Urea (UREA) | Magnesium (MAGN) |
| Volume (VOLUME) | Potassium (K+) |
| Color (COLOR) | Sodium (Na+) |
| Appearance (APP) | Total bilirubin (TOT. BIL) |
| | Total cholesterol (CHOL) |
| | Total proteins (PROT) |
| | Triglycerides (TRIG) |
| | Urea (UREA) |

Results of in vivo studies and histopathology. All 10 rat in vivo studies were successfully conducted. Sufficient urine could be collected from nearly all animals terminated at day 3, 7, 14, 21 and 22. Only animals, for which complete datasets (histopathology of kidney, urinary clinical chemistry, urinary protein biomarkers, clinical chemistry of blood, plasma protein biomarkers, mRNA biomarkers in kidney) were available were analyzed and are reported here. In total, data from 739 animals were analyzed, including 447 animals treated with nephrotoxicants, 188 animals treated with vehicles and 104 animals treated with hepatotoxicants. For nine samples, no urinary Kim-1 measurements were available; for 84 samples no blood Kim-1 measurements were available. Those samples were excluded for the Kim-1 analyses but were included for the analyses of other parameters and biomarkers.

In FIG. 2, the distributions of grades of the histopathology assessment are shown. The predominance of grade 1 and grade 2 findings and the absence of grade 5 lesions indicate that the goal of inducing mainly mild nephrotoxicity has been achieved. The considerable number of grade 1 and some grade 2 findings in the vehicle-dosed and the hepatotoxicant-dosed animals indicates the level of sensitivity of the histopathology assessment performed in this project. No significant dose-dependent nephrotoxicity was induced by the hepatotoxicants. In FIG. 3 a detailed list of all reported localized lesions, including the number of occurrences for each grade, separated by nephrotoxicant-dosed animals and the control animals (vehicle-dosed and hepatotoxicant-dosed) is shown. Seventy-five different localized finding were observed.

Figure 4:
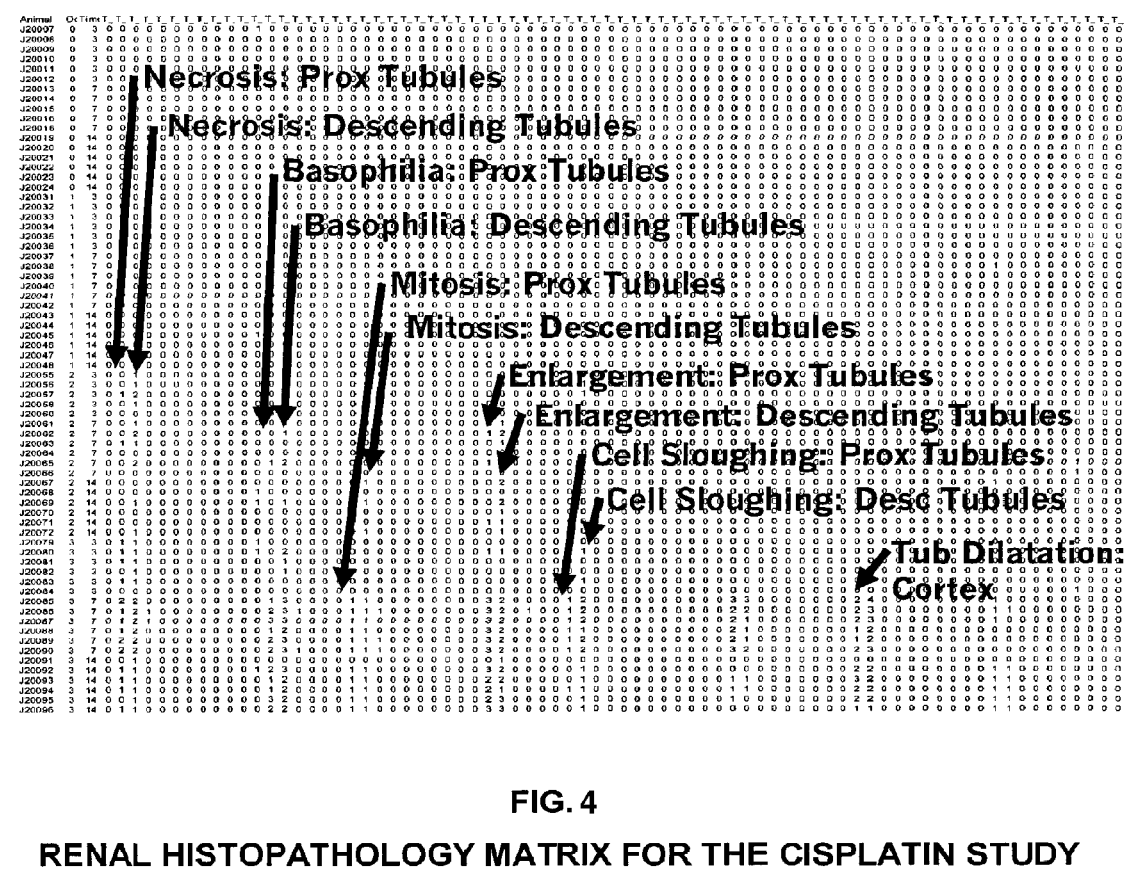

The different types of lesions were usually not observed in an isolated fashion, but typically in a highly correlated manner representing different molecular processes. In FIG. 4, all histopathology findings are shown for the cisplatin study. The processes do not affect single isolated segments of the nephron, but several segments in a correlated way (e.g. proximal tubules and descending straight tubules). In addition, a logical sequence of molecular processes along the dose- and time-ordered animals can be observed. Necrosis as a consequence of damage is seen, and then regeneration processes such as basophilia and mitosis are seen, whereas secondary processes occur in parallel (e.g., enlargement of tubules, tubular dilatation, cellular sloughing, etc.).

For the qualification of biomarkers there are two consequences: First, an appropriate level of localization detail should be found that corresponds best to the expression of a biomarker. Second, single histopathology descriptions should be integrated into molecular processes, which correspond to the molecular events triggering the expression of the biomarkers. Thus, the localized lesions were here integrated into 10 different processes, whereby for each sample the highest grade of the corresponding localized lesions was assigned to the integrated pathology. In particular following 10 pathology processes are investigated:

1. Proximal tubular damage: Lesions with a grade 1 ("minimal", "very few", "very small") or higher of the types "necrosis", "apoptosis" or "tubular cell sloughing" localized in any of the tubular segments S1, S2 or S3 or in non-localizable.

2. Glomerular alterations/damage: Lesions with a grade 1 ("minimal", "very few", "very small") or higher of the types "mesangial cell proliferation", "mesangial cell enlargement", "glomerular vacuolization" or "interstitial Bowman's capsule fibrosis".

3. Tubular damage/regeneration/dilatation: Lesions with a grade 1 ("minimal", "very few", "very small") or higher of the types "necrosis", "apoptosis", "tubular cell sloughing", "basophilia", or "mitosis increase" localized in any of the tubular segments S1, S2, S3, loop of Henle, thick ascending tubules, distal tubules, or collecting ducts or non-localizable or "tubular dilatation" in cortex, medulla or papilla.

4. Glomerular alterations/damage or tubular damage/regeneration/dilatation: Lesions with a grade 1 ("minimal", "very few", "very small") or higher of the types "mesangial cell proliferation", "mesangial cell enlargement", "glomerular vacuolization" or "interstitial Bowman's capsule fibrosis" or of the types "necrosis", "apoptosis", "tubular cell sloughing", "basophilia", or "mitosis increase" localized in any of the tubular segments S1, S2, S3, loop of Henle, thick ascending tubules, distal tubules, or collecting ducts or non-localizable or "tubular dilatation" in cortex, medulla or papilla.

5. Thick ascending tubular damage/regeneration: Lesions with a grade 1 ("minimal", "very few", "very small") or higher of the types "necrosis", "apoptosis", "basophilia", or "mitosis increase" localized in the thick ascending tubules.

6. Distal tubular damage/regeneration: Lesions with a grade 1 ("minimal", "very few", "very small") or higher of the types "necrosis", "basophilia", or "mitosis increase" localized in the distal tubules.

7. Collecting Duct damage/regeneration: Lesions with a grade 1 ("minimal", "very few", "very small") or higher of the types "necrosis", "apoptosis", "tubular cell sloughing", or "basophilia", in the collecting ducts.

8. Tubular Mineralization: Lesions with a grade 1 ("minimal", "very few", "very small") or higher of the type "intratubular casts—mineralization" localized in any of the tubular segments S1, S2, S3, loop of Henle, thick ascending tubules, distal tubules, or collecting ducts.

9. Intratubular Hyaline Casts: Lesions with a grade 1 ("minimal", "very few", "very small") or higher of the type "intratubular Casts—Hyaline (proteinaceous, pigmented)" localized in any of the tubular segments S1, S2, S3, loop of Henle, thick ascending tubules, distal tubules, or collecting ducts.

10. Juxtaglomerular Apparatus Hypertrophy: The pathologies observed in the liver of the animals of the 10 studies are listed in FIG. 5.

Description of analytics. Protein biomarkers were measured by validated multiplexed protein assays developed by and available from RulesBasedMedicine (Texas, USA). Clinical chemistry parameters (e.g. BUN, NAG, Creatinine, and LDH) were measured with standard clinical chemistry assays (ADVIA 1650 device). mRNA biomarkers were measured with TaqMan Gene Expression Assays from Applied Biosystems on Low Density Arrays on an Applied Biosystems 7900HT real-time PCR instrument. The mRNA had been extracted from half a kidney using standard procedures.

Description of data pre-processing. The concentration values of the biomarkers obtained from the analytical devices were pre-processed according to following steps: (1) concentration values, which were above the upper limit of quantitation, were replaced by the upper limit of quantitation; (2) concentration values, which were below the lower limit of quantitation, were replaced by the lower limit of quantitation; (3) urinary biomarkers were normalized to the concentration of urinary creatinine by dividing each sample by the corresponding urinary creatinine value; and (4) to express the data as fold-changes, each value was divided by the arithmetic average of the time-matched and study-matched control group (usually 6 animals).

Description of data analysis. The quantitative analyses of the data were all based on receiver operator characteristic analyses (ROC). In a ROC analysis the decision threshold is systematically varied for a binary decision problem (e.g. controls versus diseased animals) and the true positives (sensitivity) are plotted versus the true negatives (1-specificity). The area under the curve (AUC) is a measure of the diagnostic power combining sensitivity and specificity into one value, whereby a random discriminator corresponds to an AUC of 0.5 and a perfect discriminator to 1. The calculation of the AUC was performed by using trapezoidal integration as described by Bradley A P, *Pat. Recogn.* 30(7):1145-1159 (1997). The standard error of the AUC was calculated from the standard error of the Wilcoxon statistic as described by Bradley (1997).

As an application example out of the ROC analysis for a given biomarker and pathology, a threshold for the biomarker/pathology was established for a predefined minimum specificity following way:

For a given minimum specificity (e.g. 95%) first of all the lowest possible exact specificity above or at the minimum specificity was determined. For that exact specificity, the threshold with the highest corresponding sensitivity was selected. The algorithm does not look, if higher specificities for this sensitivity are possible by further varying the threshold. For this threshold, the corresponding specificity and sensitivity are reported herein.

For the analysis of the data, following definitions of control animals and diseased animals were used: (a) Control group: Animals dosed with vehicles or hepatotoxicants, and which do not show the lesion investigated. (b) Diseased group: Animals dosed with nephrotoxicants, and which were assigned a grade of 1 or higher for the lesion of interest at the histopathology assessment.

Hepatotoxicant-dosed animals are included into the control group to test the specificity of the markers versus other hepatotoxic changes and due to the fact that no dose-related nephrotoxicity was observed in these studies.

Animals that were dosed but did not show any lesion or only other lesions (other than the specific histopathology context of interest) were left out for the ROC considering that these animals are not "clean". This group of animals represents an undefined state especially when a molecular response is earlier and faster than a histopathological manifestation. In that case it cannot be decided, if (1) a single histopathology slide of one kidney is not representative for the overall state of the kidney (false negative histopathology); (2) the molecular response is earlier/more sensitive than histopathology, a so-called prodromal state; or (3) the animals are false positives if histopathology would be the only truth (false positive biomarker). The most conservative way of treating these animals is to exclude these animals from any analysis as no definitive assignment to any group can be made.

Results for biomarkers and pathologies of interest to monitor renal injury. The results of the ROC analysis combining histopathology, study information and biomarker values are shown for the most interesting renal pathologies and biomarkers in FIG. 6.

Figure 7A:
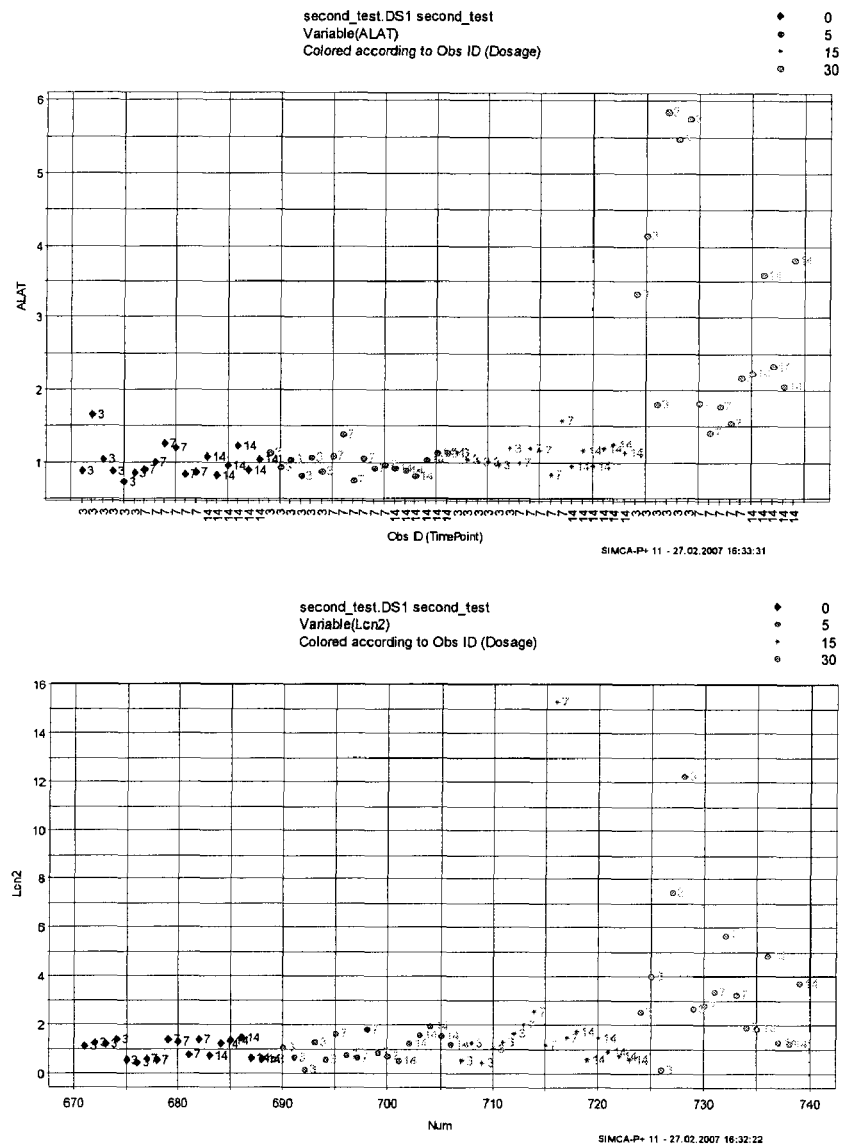
FIG. 7 is a set of scatter plots showing an assessment of hepatotoxicity by different protein biomarkers. The biomarkers were obtained from animals to which vehicle or different doses of the hepatotoxicant ANIT (alpha-naphtylisothiocyanate) was administered. In this study dose-related histopathology findings in the liver but not in the kidney were observed. In the plots the relative concentration levels (fold changes versus controls) are shown. The dose-levels are represented by the different color shadings, the time points of sampling are represented by the labels. The biomarker levels correlate well with the dose and thus with the dose-related hepatotoxicity. The biomarkers represented in these plots are ALAT measured in plasma (FIG. 7A top), lipocalin-2 measured in plasma (FIG. 7A bottom), GST-mu measured in plasma (FIG. 7B top) and lipocalin-2 measured in urine (FIG. 7B bottom).
Figure 7B:
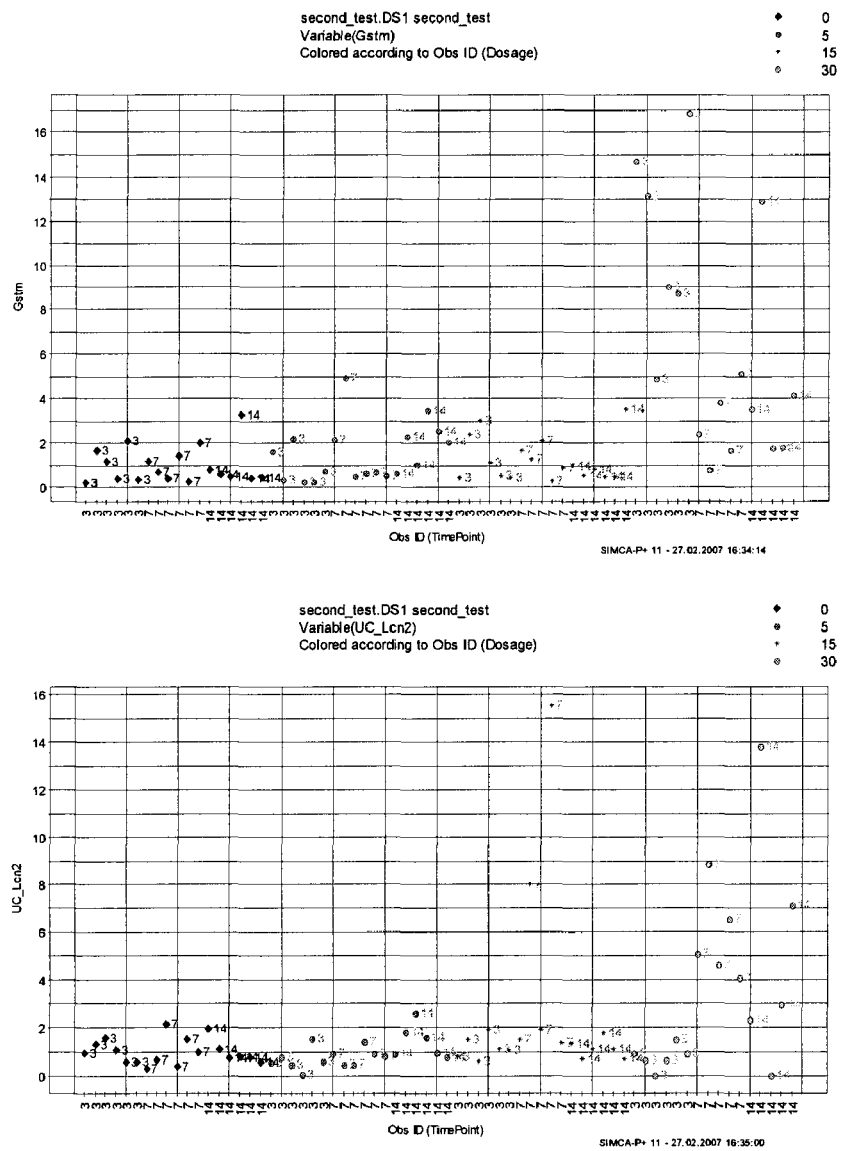

Proteins and clinical chemistry parameters to monitor and identify liver injury. The biomarkers were obtained from animals to which vehicle or different doses of the hepatotoxicant ANIT (alpha-Naphtylisothiocyanate) was administered. See, FIG. 7. Dose-related histopathology findings in the liver but not in the kidney were observed. In the plots the relative concentration levels (fold changes versus controls) are shown. The dose-levels are represented by the different color shadings, the time points of sampling are represented by the labels. The biomarker levels correlate well with the dose and thus with the dose-related hepatotoxicity. The biomarkers represented in these plots are the current standard ALAT measured in plasma (FIG. 7A top) and the new markers Lipocalin-2 measured in plasma (FIG. 7A bottom), GST-mu measured in plasma (FIG. 7B top) and Lipocalin-2 measured in urine (FIG. 7B bottom).

Figure 8A:
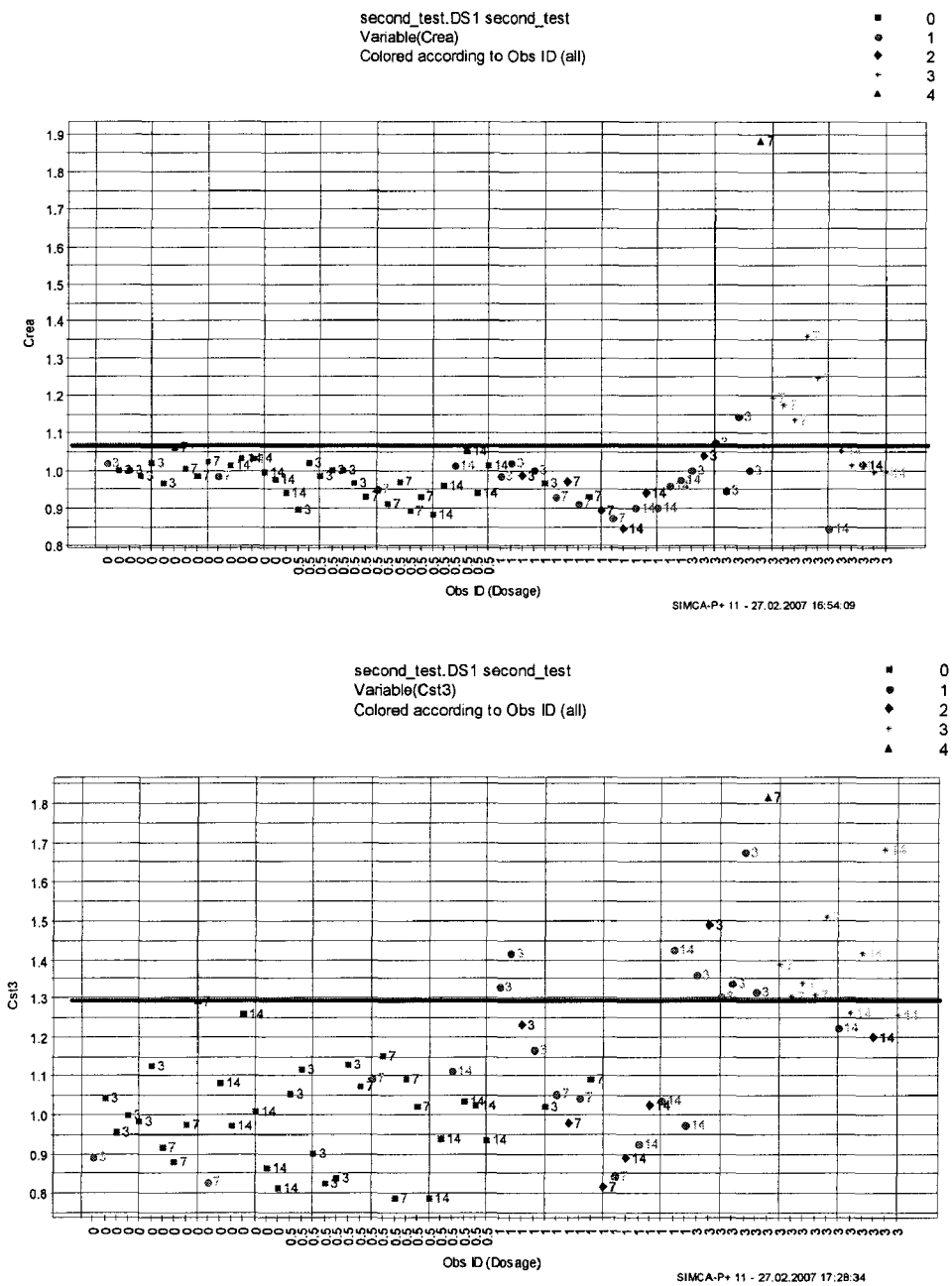
FIG. 8 is a set of scatter plots showing an assessment of kidney injury by different protein biomarkers and clinical chemistry parameters. The biomarkers were obtained from animals to which vehicle or different doses of the nephrotoxicant cisplatin were administered. In the plots the relative concentration levels (fold changes versus controls) are shown. The dose-levels are represented as labels of the x-axis, the time points of sampling are represented by as labels of the samples. The samples are color shaded by the highest grade of histopathology finding observed in kidney. The horizontal bar indicates the highest biomarker level observed for case control animals (vehicle dosed animals without histopathology finding in kidney). Protein levels higher than the bar are significantly increased (100% specificity for case controls). The different clinical parameters and proteins detect kidney injury with different sensitivity. Creatinine measured in serum, which is the current standard peripheral test for kidney injury and kidney function, is the least sensitive method (FIG. 8A top). Cystatin C measured in plasma (FIG. 8A bottom), Kim-1 measured in urine (FIG. 8B top), lipocalin-2 measured in urine (FIG. 8B bottom), osteopontin measured in urine (FIG. 8C top) and clusterin measured in urine (FIG. 8C bottom) identify more animals with significant kidney findings.
Figure 8B:
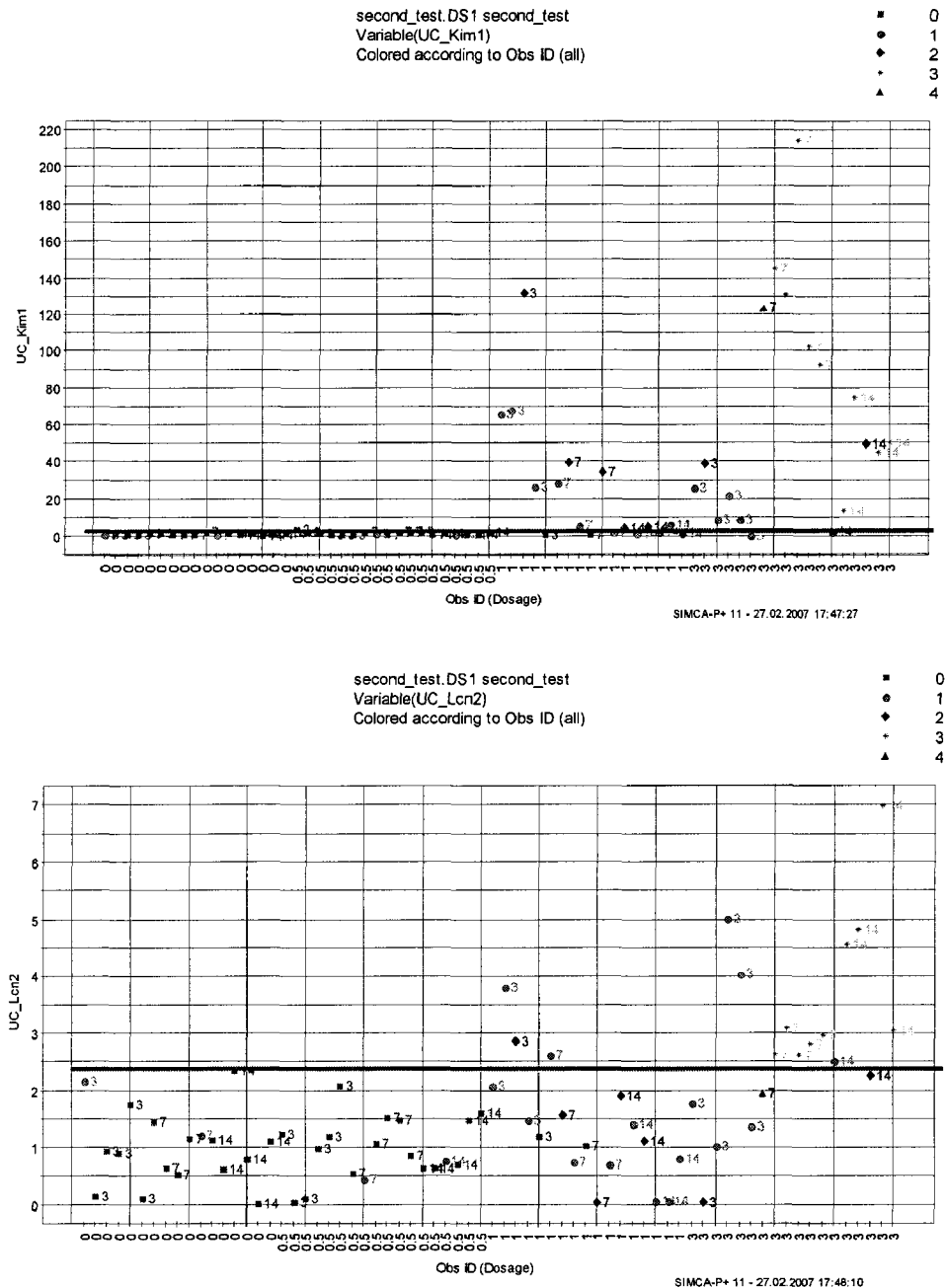
Figure 8C:
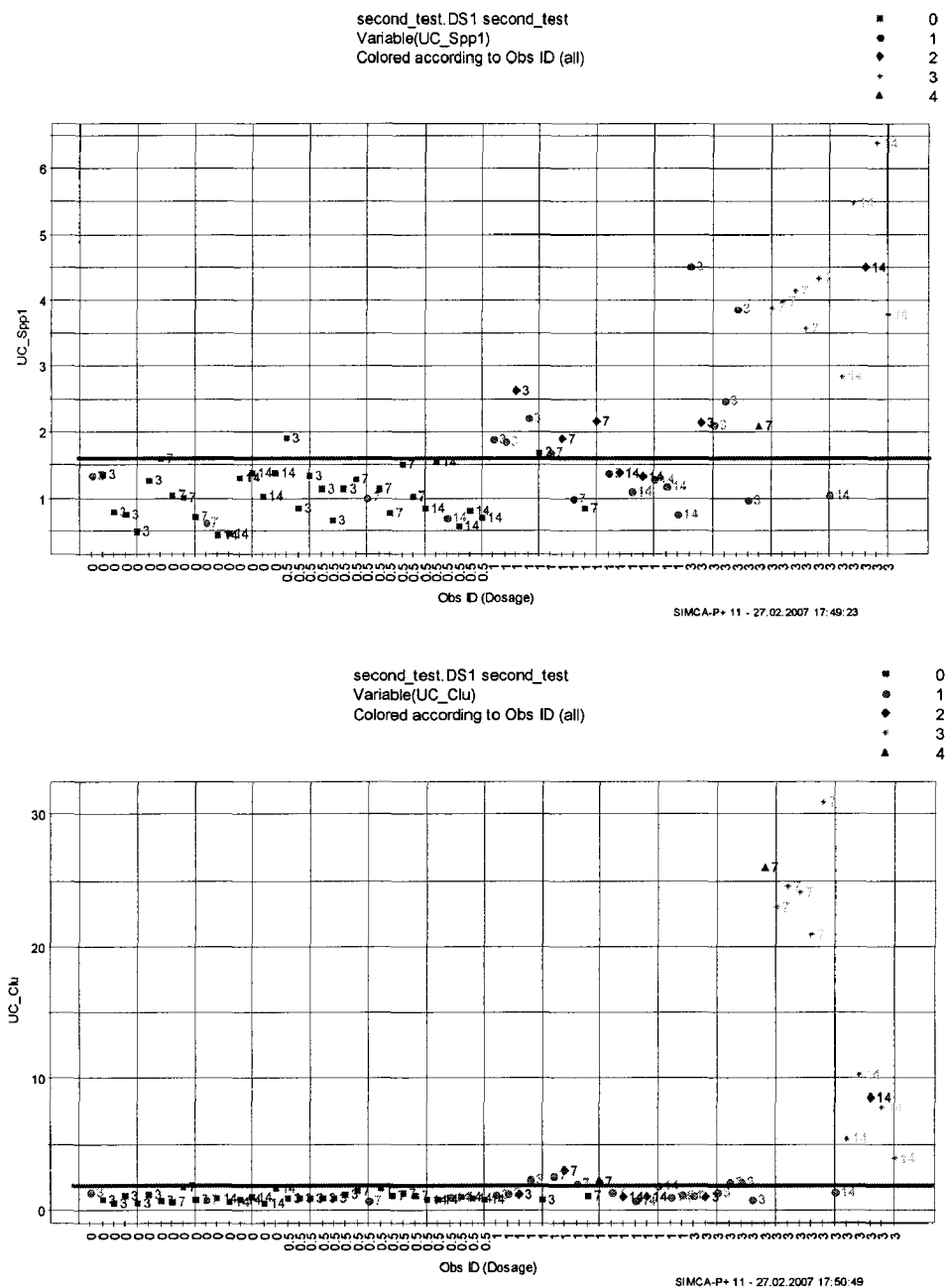

Proteins and clinical chemistry parameters to monitor and identify kidney injury. The biomarkers were obtained from animals to which vehicle or different doses of the nephrotoxicant Cisplatin was administered. See, FIG. 7. In the plots the relative concentration levels (fold changes versus controls) are shown. The dose-levels are represented as labels of the x-Axis, the time points of sampling are represented by as labels of the samples. The samples are color shaded by the highest grade of histopathology finding observed in kidney. The horizontal bar indicates the highest biomarker level observed for case control animals (vehicle dosed animals without histopathology finding in kidney). Protein levels higher than the bar are significantly increased (100% specificity for case controls). Also, other thresholds are possible. Specific thresholds for 95% specificity are given in FIG. 6. The different clinical parameters and proteins detect kidney injury with different sensitivity. Creatinine measured in serum, which is the current standard peripheral test for kidney injury and kidney function, is the least sensitive method (FIG. 8A top). Cystatin C measured in plasma (FIG. 8A bottom), Kim-1 measured in urine (FIG. 8B top), lipocalin-2 measured in urine (FIG. 8B bottom), osteopontin measured in urine (FIG. 8C top) and clusterin measured in urine (FIG. 8C bottom) identify more animals with significant kidney findings.

Figure 9A:
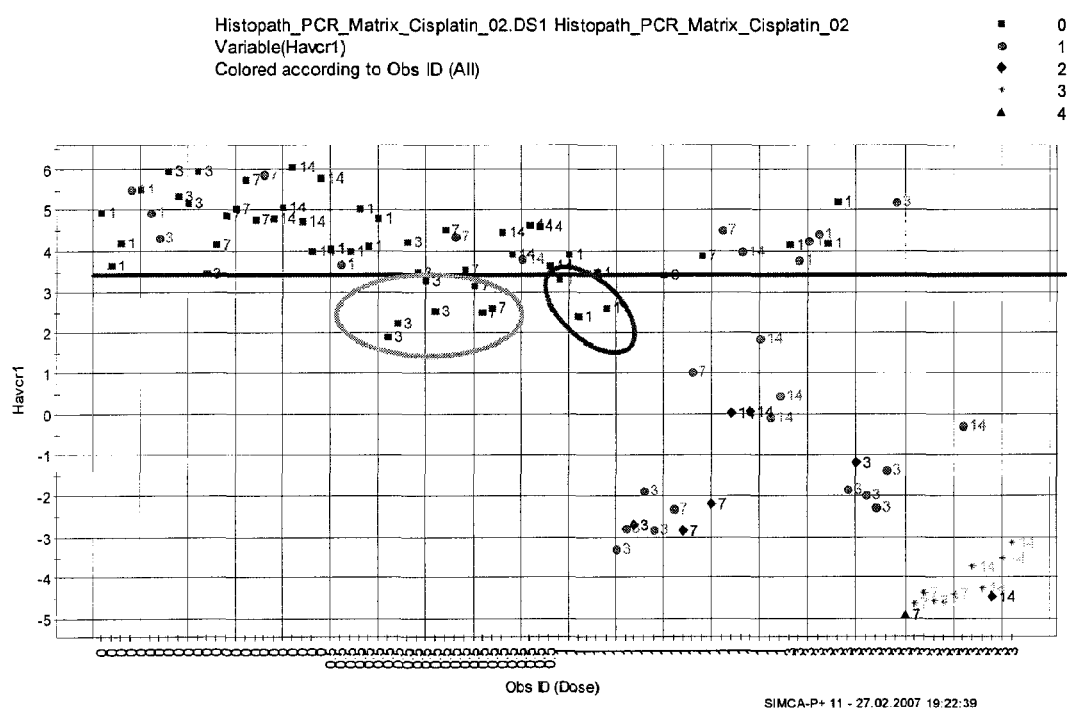
FIG. 9 is a set of scatter plots showing an assessment of kidney injury by transcription of different genes in mRNA from kidney. The biomarkers were obtained from animals to which vehicle or different doses of the nephrotoxicant cisplatin were administered. In the plots the expression values (Ct values referenced to Polr2g) are shown. The dose-levels are represented as labels of the x-Axis, the time points of sampling are represented by as labels of the samples. The samples are color shaded by the highest grade of histopathology finding observed in kidney. The horizontal bar indicates the highest expression (lowest value in the plot) observed for control animals. Values below the bar correspond to significantly increased expression levels (100% specificity for non-dosed animals). Both Kim-1 (FIG. 9A) and Cyr61 (FIG. 9B) can detect kidney injury earlier (at earlier time points) and in a more sensitive way (at lower dose levels) than histopathological examination.
Figure 9B:
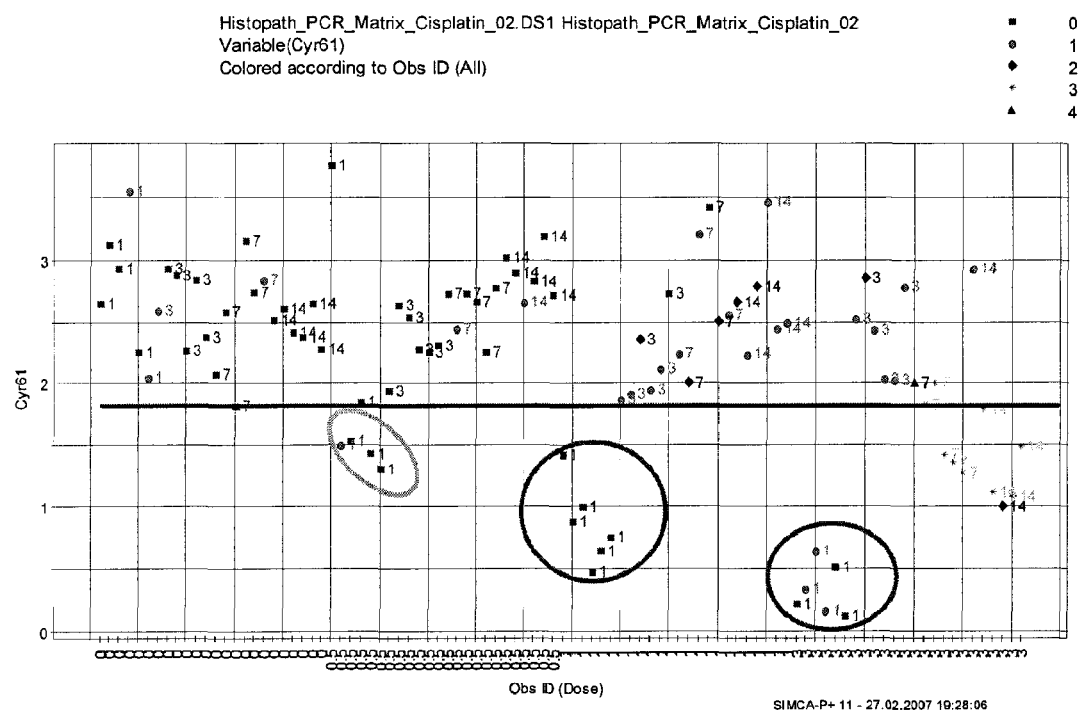

Gene transcription to monitor and idents kidney injury. The biomarkers were obtained from animals to which either vehicle or the nephrotoxicant cisplatin was administered. See, FIG. 9. In the plots the expression values (Ct values referenced to Polr2g) are shown. The dose-levels are represented as labels of the x-Axis, the time points of sampling are represented by as labels of the samples. The samples are color shaded by the highest grade of histopathology finding observed in kidney. The horizontal bar indicates the highest expression (lowest value in the plot) observed for control animals. Values below the bar correspond to significantly increased expression levels (100% specificity for non-dosed animals). Also, other thresholds are possible. Specific thresholds for 95% specificity are proposed in FIG. 6. Both Kim-1 (FIG. 9A) and Cyr61 (FIG. 9B) can be used to detect kidney injury earlier (at earlier time points) and in a more sensitive way (at lower dose levels) than histopathological examination.

Embodiments and aspects of the invention. Using mathematical operations and data described herein, the invention provides the following embodiments:

The invention provides methods for diagnosing, predicting and classifying renal toxicity and/or liver toxicity by the use of single biomarkers of the invention or combinations of biomarkers (clinical chemistry parameters, proteins, mRNA transcription) in biological matrices (urine, blood, mRNA from kidney and blood). The invention also provides methods for diagnosing, predicting and classifying histopathology findings, combinations of histopathology findings and mechanisms manifested by histopathology findings in kidney, in liver or in kidney and liver with the help of measurements of single biomarkers or combinations of biomarkers (clinical chemistry parameters, proteins, mRNA transcriptions) in single biological matrices or in different biological matrices. In the use of the invention, a histopathological finding in the kidney corresponds to a renal toxicity or renal disease symptom and a histopathological finding in the liver corresponds to a liver toxicity or liver disease symptom.

Thus, the level of expression, or the level of function, of a marker in an individual can be determined to thereby select appropriate agent for therapeutic or prophylactic treatment of the individual. This knowledge, when applied to dosing or drug selection, can avoid adverse reactions or therapeutic failure, and thus enhance therapeutic or prophylactic efficiency when treating a subject with a modulator of expression of a marker. See WO 2004/005544, incorporated herein by reference.

The invention further provides methods for diagnosing, predicting and classifying single biomarkers or combinations of biomarkers in biological matrices with the help of single biomarkers or combinations of biomarkers in the biological matrices.

The invention still further provides methods for predicting the fate of individuals (e.g. survival rate) with the help of measurements of the biomarkers of the invention in biological matrices.

In one aspect, the invention shows that the biomarkers of the invention can be used to predict, classify, and diagnose histopathology findings, combinations of histopathology findings, and mechanisms manifested by histopathology findings in kidney, in liver or in kidney and liver, with higher sensitivity and specificity, at earlier time point and at lower dose levels than other biomarkers.

In another aspect, the invention shows that the biomarkers of the invention can be used to predict, classify, and diagnose histopathology findings, combinations of histopathology findings, and mechanisms manifested by histopathology findings in kidney, in liver or in kidney and liver in the course of the study earlier than the assessment of histopathology of liver and kidney at that time point of the study. This means that the modeling, diagnosis, classification and prediction of histopathology with the help of biomarkers are earlier, more sensitive and more specific than the assessment of histopathology itself.

The methods of the invention can be used not only with the described biomarkers of the invention, but also with degradation products thereof or combinations of the described biomarkers and degradations products. The degradation products could be peptides or peptide fragments of described proteins or mRNA fragments and degradation products of described mRNA transcriptions. Moreover, the methods of the invention can use not only the described biomarkers, but also substantially similar biomarkers, such as different isoforms, splicing variants or fragments. In some embodiments, the methods of the invention can use polymorphisms in a gene of described biomarkers of the invention.

The invention also provides for the implementation of these markers, combination of these biomarkers and the models, correlations, predictions, classification and diagnostics of the biomarkers with histopathology and other biomarkers into a device. In particular, the invention provides a test, device, assay, biomarker test, clinical test kit or diagnostic device to monitor or diagnose the state and function of the kidney or the state and function of the liver. In another embodiment, the invention provides a test, device, assay, biomarker test, clinical test kit or diagnostic device to monitor or diagnose adverse effects of drugs on the kidney or on the liver. In still another embodiment, the invention provides a test, device, assay, biomarker test, clinical test kit or diagnostic device to identify candidate agents (drugs) that do not provoke or induce adverse effects in the kidney or in the liver. In yet another embodiment, the invention provides a test, device, assay, biomarker test, clinical test kit or diagnostic device to determine if an individual responds to therapy with respect to kidney toxicity, liver toxicity or kidney and liver toxicity.

The components of the kit may be for the measurement of gene expression by Northern blot analysis, reverse transcription PCR or real time quantitative PCR, branched DNA, nucleic acid sequence based amplification (NASBA), transcription-mediated amplification, ribonuclease protection assay, or microarrays. Another particular embodiment provides a kit, wherein the means for determining the level of gene expression or gene expression product comprise at least one antibody specific for a protein encoded by the marker gene selected among the biomarkers of the invention. The antibody is preferably selected among polyclonal antibodies, monoclonal antibodies, humanized or chimeric antibodies, and biologically functional antibody fragments sufficient for binding of the antibody fragment to the marker. Particularly preferred are immunoassay methods for determining the level of gene expression.

In another preferred embodiment of the invention a kit is provided which further comprises means for obtaining a body sample of the individual, particularly plasma or urine. A particularly preferred embodiment further comprises a container suitable for containing the means for determining the level of gene expression and the body sample of the individual. In another preferred embodiment the kit further comprises instructions for use and interpretation of the kit results.

In several embodiments, the invention provides tests, devices, assays, biomarker tests, clinical test kits or diagnostic devices (i) to identify candidate agents (drugs) that ameliorate one or several symptoms of kidney toxicity; (ii) to identify candidate agents (drugs) that ameliorate one or several symptoms of liver toxicity; (iii) to compare the renal toxicity potential of two agents (drugs); and (iv) to compare the liver toxicity potential of two agents (drugs).

For example, the effectiveness of an agent to affect marker expression can be monitored in clinical trials of subjects receiving treatment for renal disease or toxicity. In a preferred embodiment, the invention provides a method for monitoring the effectiveness of treatment of a subject with an agent (e.g., an agonist, antagonist, peptidomimetic, protein, peptide, nucleic acid, small molecule, or other drug candidate) comprising the steps of: (i) obtaining a pre-administration sample from a subject prior to administration of the agent; (ii) detecting the level of expression of one or more selected markers of the invention in the pre-administration sample; (iii) obtaining one or more post-administration samples from the subject; (iv) detecting the level of expression of the markers in the post-administration samples; (v) comparing the level of expression of the markers in the pre-administration sample with the level of expression of the markers in the post-administration sample or samples; and (vi) altering the administration of the agent to the subject accordingly. For example, modified administration of the agent can be desirable to increase expression of the markers to I higher levels than detected, i.e., to increase the effectiveness of the agent. Alternatively, increased/decreased administration of the agent can be desirable to increase/decrease the effectiveness of the agent, respectively.

In a particular embodiment, the invention provides a method for identifying candidate agents for use in the treatment of renal toxicity comprising the steps of (a) contacting a sample of a kidney tissue subject to toxicity with a candidate agent; (b) determining from the kidney tissue the level of gene expression or gene expression product, particularly protein, corresponding to one or more genes selected among of the biomarkers of the invention, to obtain a first set of value; and (c) comparing the first set of value with a second set of value corresponding to the level of gene expression or gene expression product, particularly protein, assessed for the same genes and under identical condition as for step (b) in a kidney tissue subject to toxicity not induced by the candidate agent.

In another particular embodiment, the invention provides a method for identifying candidate agents that do not provoke or induce renal toxicity comprising the steps of: (a) contacting a sample of a kidney tissue not subject to toxicity with a candidate agent; (b) determining from the kidney tissue the level of gene expression or gene expression product, particularly protein, corresponding to one or more genes selected among the biomarkers of the invention, to obtain a first set of value; and (c) comparing the first set of value with a second set of value corresponding to the level of gene expression or gene expression product, particularly protein, assessed for the same genes and under identical condition as for step (b) in a kidney tissue not subject to toxicity.

In another particular embodiment, the invention provides a method for comparing renal cytotoxic potentials of two drug candidates comprising the steps of (a) contacting a sample of a kidney tissue not subject to toxicity with a first drug candidate, and determining from the kidney tissue levels of gene expression or gene expression product, particularly protein, corresponding to one or more genes selected among the biomarkers of the invention to obtain a first value; and (b) contacting a sample of a kidney tissue not subject to toxicity with a second drug candidate, and determining from the kidney tissue level of gene expression corresponding to one or more genes selected among the biomarkers of the invention to obtain a second value; and (c) comparing the first value with the second value.

In other embodiments, the invention provides a therapeutic method for treating renal and/or liver toxicity in an individual patient by administrating a therapeutically effective amount of a modulating compound that modulates in the liver and/or kidney the synthesis, expression or activity of one or several genes, gene expression products or proteins listed in TABLE 1 so that at least one symptom or renal and/or liver toxicity is ameliorated.

In a particular aspect of the invention, a method is provided for both prophylactic and therapeutic methods of treating a subject having, or at risk of having, a kidney disorder or renal toxicity. Administration of a prophylactic agent can occur prior to the manifestation of symptoms characteristic of the kidney disorder, such that development of the kidney disorder is prevented or delayed in its progression.

In another particular embodiment, the invention provides a method for treating or preventing renal toxicity in an individual comprising the step of administering to said individual a therapeutically effective amount of a modulating compound that modulates in the kidney the synthesis, expression or activity of one or more of the genes or gene expression products, particularly protein, of the group of genes of the biomarkers of the invention, so that at least one symptom of renal toxicity is ameliorated.

In yet another particular embodiment, the invention provides a method for treating renal toxicity in an individual comprising the step of administering to said individual a therapeutically effective amount of a modulating compound that modulates in the kidney the synthesis, expression or activity of one or more of the genes or gene expression products, particularly protein, of the group of genes of the biomarkers of the invention, so that at least one symptom of renal toxicity is ameliorated.

In a further embodiment, the invention provides a method for treating renal toxicity in an individual under treatment with a cytotoxic agent is provided, comprising the step of administering to said individual a therapeutically effective amount of a modulating compound that modulates in the kidney the synthesis, expression or activity of one or more of the genes or gene expression products, particularly protein, of the group of genes of the biomarkers of the invention, so that at least one symptom of renal toxicity is ameliorated.

The invention provides a method for identifying other new biomarkers for diagnosing, predicting, classifying or monitoring liver toxicity and/or kidney toxicity or symptoms thereof with the help of the markers, combination of the biomarkers and models, correlations, predictions, classifications and diagnostics of this invention.

One particular advantage of the above methods, i.e., methods (i) for identifying candidate agents, (ii) for comparing renal cytotoxic potentials of two drug candidates and (iii) for identifying candidate agents that do not provoke or induce renal toxicity, is that they an be performed in vitro. The kidney tissues that are used are preferably obtained from a cultured kidney tissue or cells that have been contacted with a cytotoxic agent. The kidney tissue can also be a kidney sample of an individual subject to renal toxicity, but this may limit broad in-vitro applications of such methods.

Thus, the invention provides a test which measures the above mentioned biomarkers in cultured kidney tissue or cells to predict, classify or diagnose kidney toxicity and/or liver toxicity in vivo. This may be a single or collection of kidney or liver cells such as the human kidney epithelial 293Tcells HK2 cell lines, human embryonic kidney cell lines, or human embryonic liver cell lines for instance. Changes in the expression profile from a baseline profile while the cells are exposed to various modifying conditions, such as contact with a drug or other active molecules can be used as an indication of such effects.

Cultured kidney tissue or cells may be advantageously based on an in vivo animal model that mimics human cellular and tissues disorders, preferably of the kidney. It may also be a single or collection of kidney cells such as the human kidney epithelial 293Tcells or a human embryonic kidney cell line, for instance. The kidney is particularly susceptible to the nephrotoxic action of drugs, because of its functional properties, including (a) the high volume of renal blood flow, which brings large amounts of toxin; (b) the large area in contact with the drug, either in the glomerulus or the tubule epithelium, which enables toxin interaction or uptake; (c) the kidney's ability to transfer active substances, which provides specific transfer mechanisms that mediate cellular uptake; (d) drug breakdown, which may occur in renal tubules and lead to the formation of toxic metabolites from non-toxic parent substances; e) the kidney's concentrating mechanisms, which can increase urinary and interstitial concentrations of non-absorbed products; the high metabolic rate of tubule cells required for normal function, which is subject to perturbation.

EQUIVALENTS

The invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The invention is to be limited only by the terms of the appended claims along with the full scope of equivalents to which such claims are entitled.

We claim:

1. A method for assessing glomerular alteration or damage of the kidney in an individual following administration of a compound suspected of causing renal toxicity comprising:

measuring the amount of $\beta$-2-microglobulin protein in a urine sample from the individual, and comparing the measured $\beta$-2-microglobulin protein amount with the corresponding amount in a healthy individual, wherein an increase in $\beta$-2-microglobulin protein in the individual administered with the compound compared to the healthy individual indicates glomerular alteration or damage of the kidney.

2. A method of assessing glomerular alteration or damage of the kidney in an individual suspected of having renal toxicity comprising:

measuring the amount of $\beta$-2-microglobulin protein in a urine sample from the individual, and comparing the measured $\beta$-2-microglobulin protein amount with the corresponding amount in a healthy individual, wherein an increase in $\beta$-2-microglobulin protein in the individual compared to the healthy individual indicates glomerular alteration or damage.

3. The method of claim 1, wherein the measuring is performed using an antibody against $\beta$-2-microglobulin protein.

4. The method of claim 1, wherein the measuring is performed by immunoassay.

5. The method of claim 1, wherein the compound is puromycin, vanomycin, doxorubicin, lithium caronate, cisplatin or FK506.

6. The method of claim 2, wherein the measuring is performed using an antibody against $\beta$-2-microglobulin protein.

7. The method of claim 2, wherein the measuring is performed by immunoassay.

* * * * *